United States Patent
Edge et al.

(12)

(10) Patent No.: US 6,610,288 B1
(45) Date of Patent: *Aug. 26, 2003

(54) PORCINE HEPATOCYTES FOR USE IN TREATMENT OF DISORDERS CHARACTERIZED BY INSUFFICIENT LIVER FUNCTION

(75) Inventors: Albert Edge, Cambridge, MA (US); J. Ryan Gunsalus, Boston, MA (US); Nezam H. Afdhal, Charlestown, MA (US)

(73) Assignees: Diacrin, Inc., Charlestown, MA (US); Trustees of Boston University, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/653,059

(22) Filed: May 24, 1996

Related U.S. Application Data

(63) Continuation-in-part of application No. 08/451,915, filed on May 26, 1995, now abandoned.

(51) Int. Cl.[7] .................... A01N 63/00; A61K 48/00; A61K 39/00; C12N 15/00
(52) U.S. Cl. ............ 424/93.2; 424/139.1; 424/184.1; 435/325
(58) Field of Search ............................ 435/240.2, 325; 424/93.1, 93.21, 93.3, 139.1, 184.1; 530/387.1, 388.85; 600/19

(56) References Cited

U.S. PATENT DOCUMENTS 5,283,058 A * 2/1994 Faustman ................. 424/88

OTHER PUBLICATIONS

Grossman (1994) Nature Genetics 6, 335–341.*
Immunology, by Janis Kuby, W. H. Freeman and Co., New York, New York, 1992, pp. 336 and 338.*
Lie et al., Immunology 64: 599–605 (1988).*
Maganto et al., Transplantation Preceedings 24(6): 2826–2827 (1992).*
Maganto, Cell Transplantation 2: 407–408 (1993).*
Adam et al Surgery 111(6): 610–616 (1992).*

* cited by examiner

Primary Examiner—Deborah Crouch
(74) Attorney, Agent, or Firm—Lahive & Cockfield, LLP; Giulio A. DeConti, Jr., Esq.; Megan E. Williams, Esq.

(57) ABSTRACT

Isolated porcine hepatocytes, isolated populations of such hepatocytes and methods for using the hepatocytes to treat subjects with disorders characterized by insufficient liver function are described. The porcine hepatocytes can be either hepatocytes isolated from adult, immature, or embryonic swine. The porcine hepatocytes can be modified to be suitable for transplantation into a xenogeneic subject, for example, by altering an antigen (e.g., an MHC class I antigen) on the cell surface which is capable of stimulating an immune response against the cell in the subject (e.g., by contact with an anti-MHC class I antibody, or a fragment or derivative thereof). The isolated porcine hepatocytes of the invention can be used to treat disorders characterized by insufficient liver function by administering the hepatocytes to a subject having such a disorder.

29 Claims, 14 Drawing Sheets

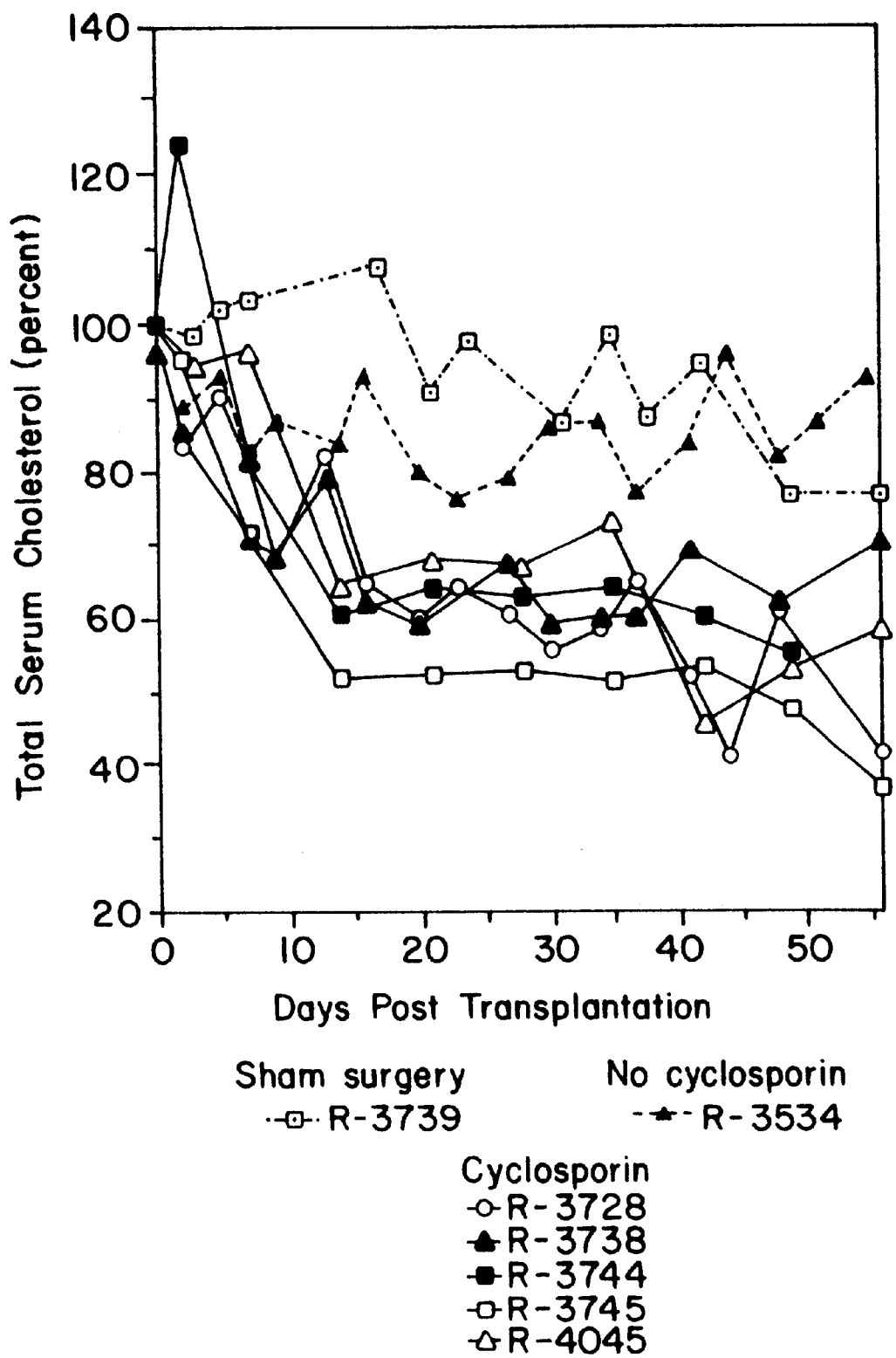

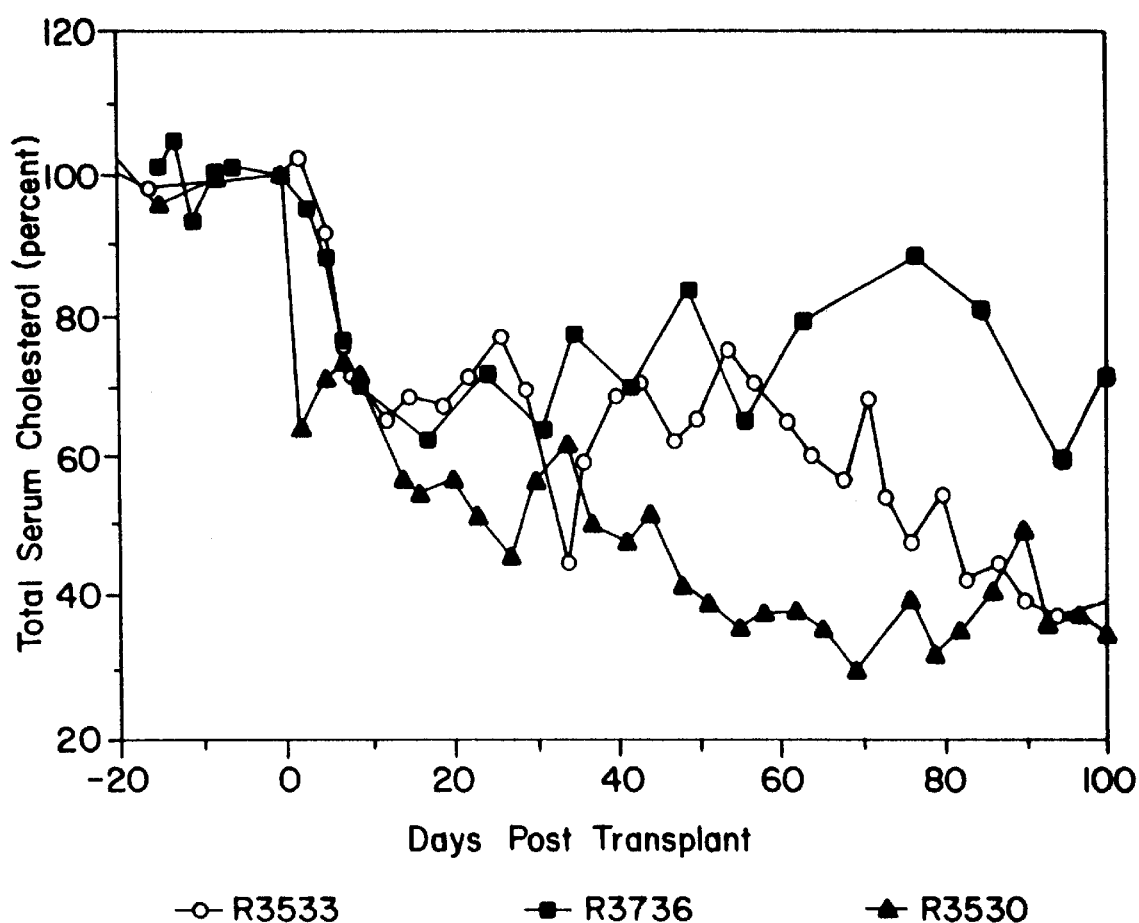

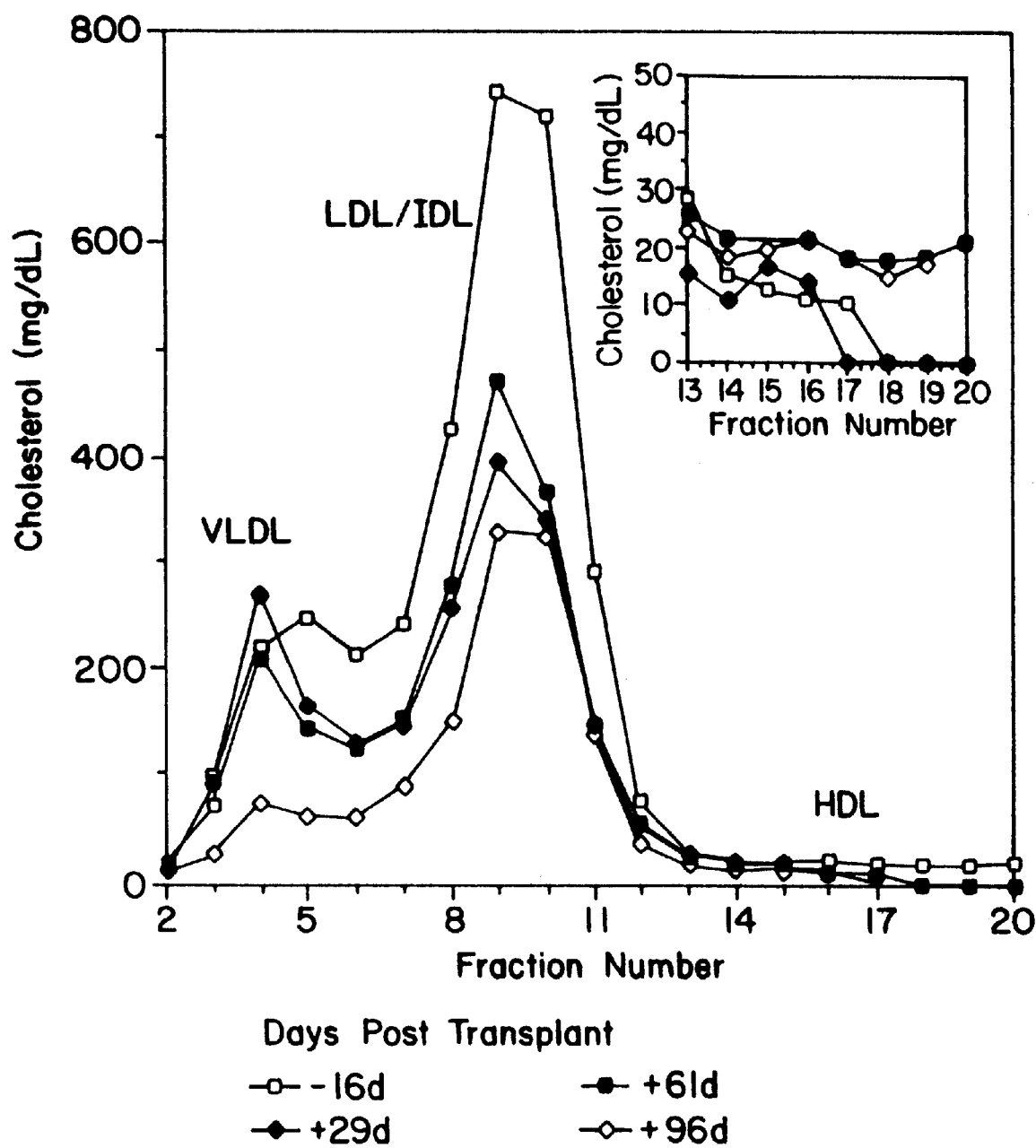

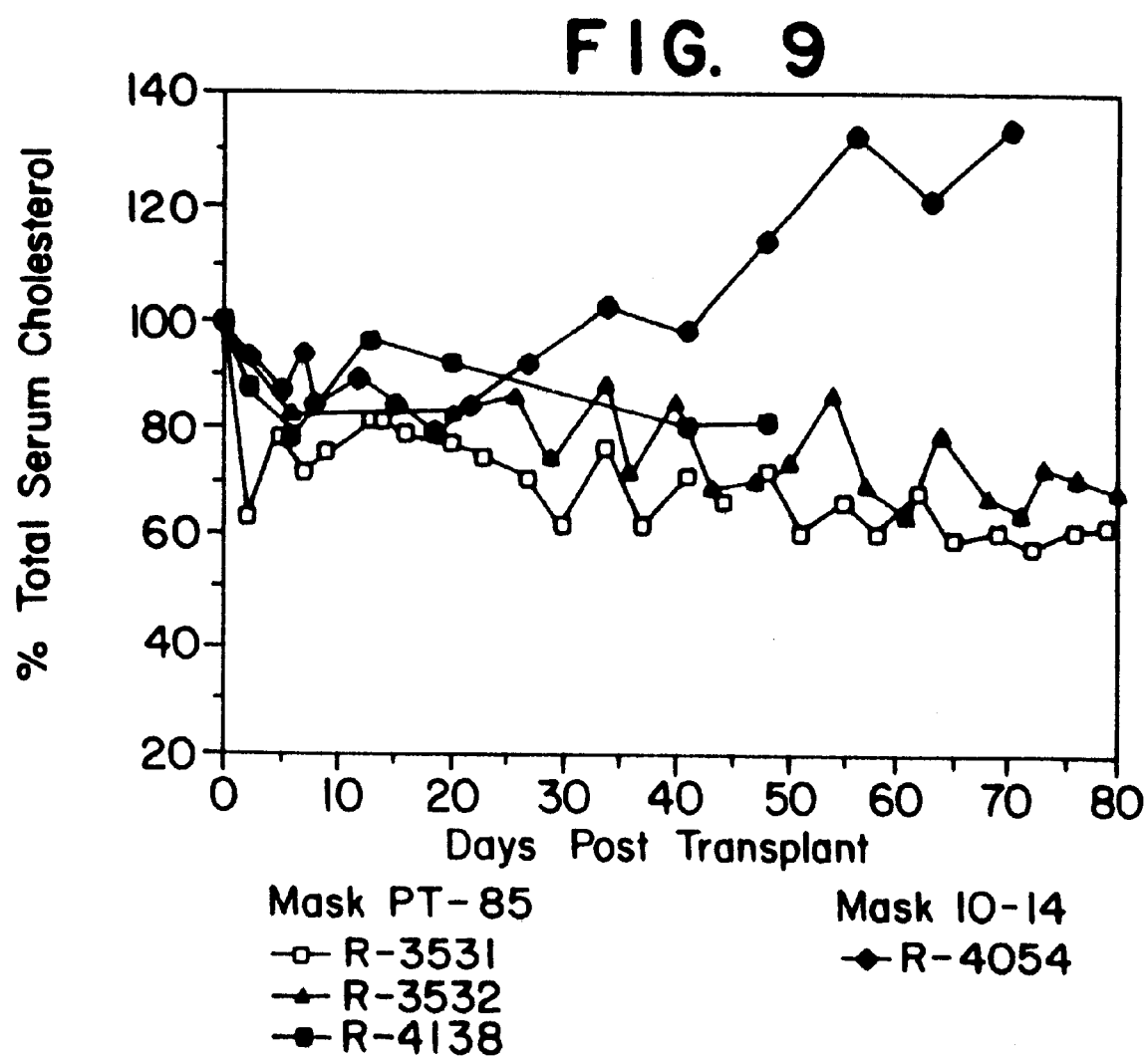

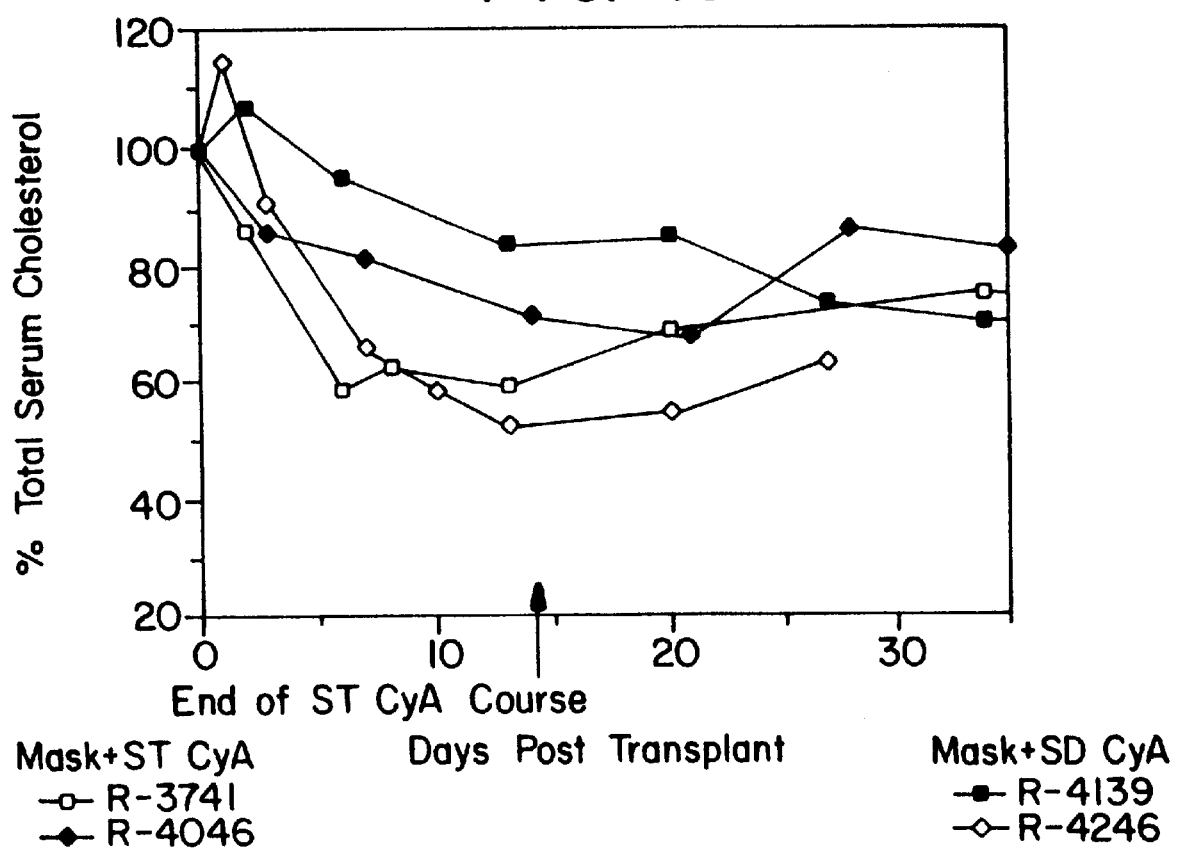

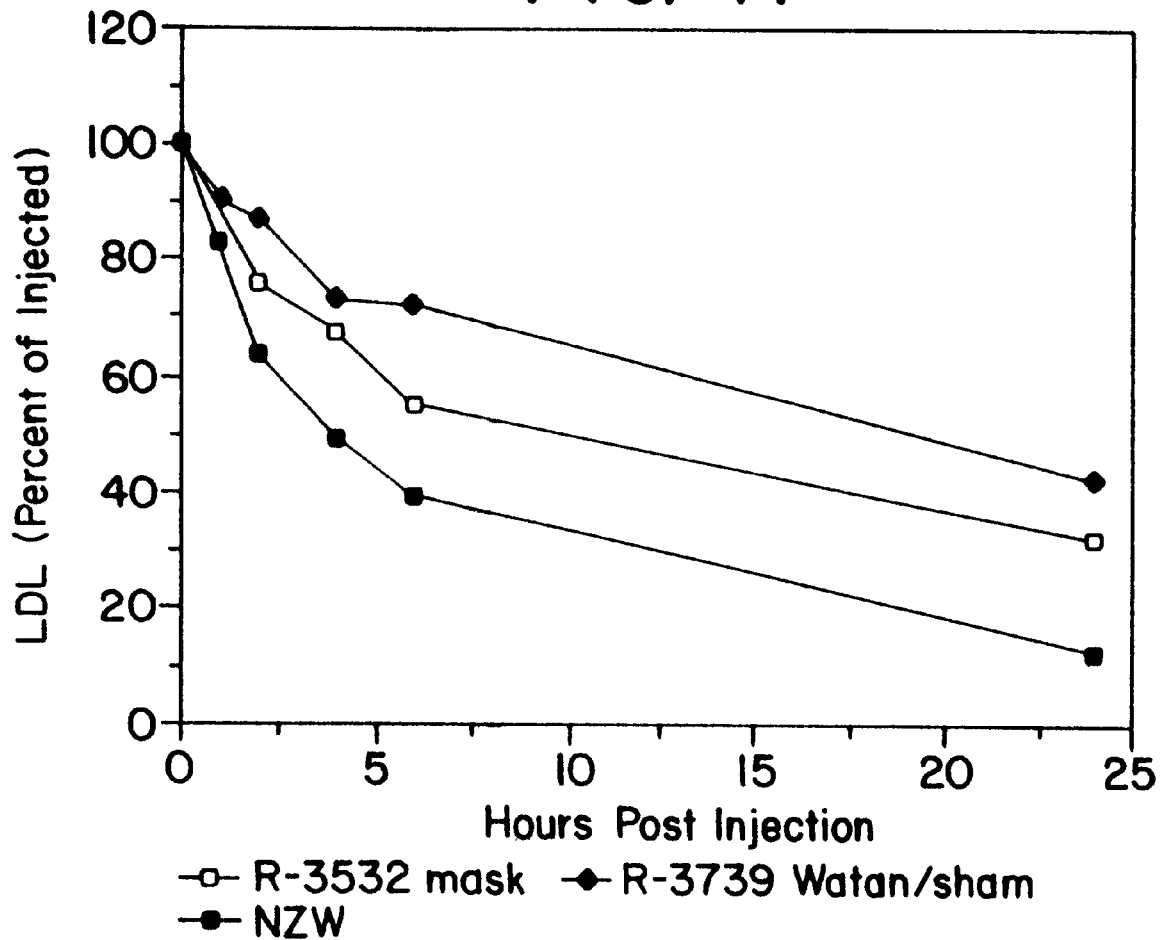

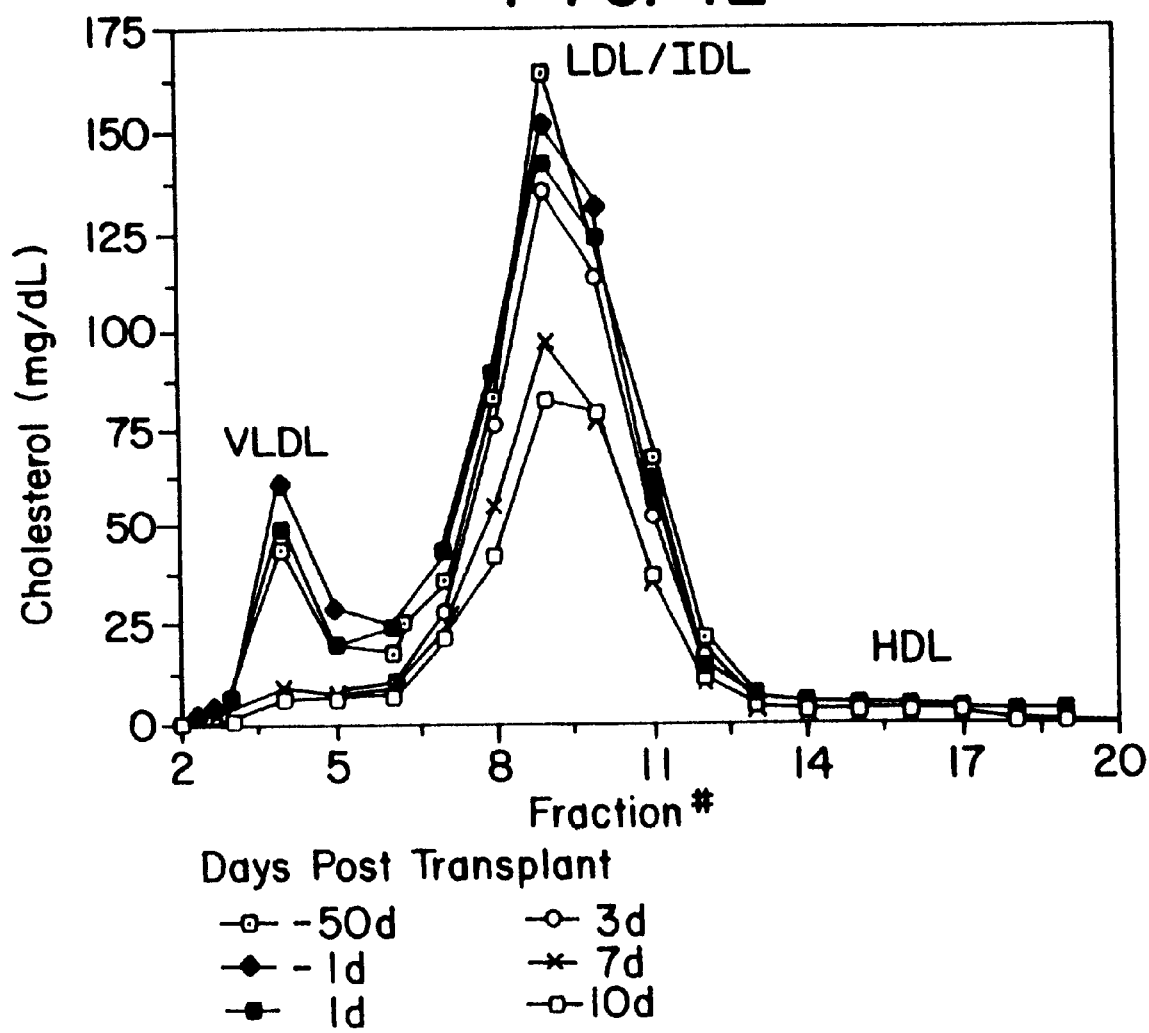

PORCINE HEPATOCYTES FOR USE IN TREATMENT OF DISORDERS CHARACTERIZED BY INSUFFICIENT LIVER FUNCTION

RELATED APPLICATIONS

This application is a continuation-in-part of U.S. Ser. No. 08/451,915, filed May 26, 1995, now abandoned the contents of which are incorporated herein by reference.

BACKGROUND OF THE INVENTION

Vulnerable to a wide variety of metabolic, circulatory, toxic, microbial, and neoplastic insults, the liver is one of the most frequently injured organs in the body. In some instances, the disease is primarily localized in liver cells. For example, primary liver diseases include hereditary disorders such as Gilbert's Syndrome, Crigler-Najjar Syndrome (either Type I or Type II), Dubin Johnson Syndrome, familial hypercholesterolemia, ornithine transcarbamoylase (OTC) deficiency, hereditary emphysema and hemophilia; viral infections such as hepatitis A, B, and non-A, non-B hepatitis; and hepatic malignancies such as hepatocellular carcinoma. Robbins, S. L. et al. (1984) Pathologic Basis of Disease (W.B. Saunders Company, Philadelphia) pp. 884–942. More often, the hepatic involvement is secondary, often to some of the most common diseases of man, such as cardiac decompensation, disseminated cancer, alcoholism, and extrahepatic infections. Robbins, S. L. et al. (1984) Pathologic Basis of Disease (W.B. Saunders Company, Philadelphia) pp. 884–942.

One of the more devastating of the above-listed liver diseases is familial hypercholesterolemia (FH). FH is a consequence of a mutation in the low density lipoprotein (LDL) receptor locus. Brown, M. S. et al. (1986) Science 232:34–47. The LDL receptor is a specific cell membrane receptor involved in the transport and metabolism of cholesterol. FH heterozygotes with one mutant allele (representing about one in 500 individuals) have, from birth, a two- to threefold elevation of plasma cholesterol leading to premature atherosclerosis and coronary heart disease in adult life. Grundy, S. M. et al. JAMA 269:3015–3023. Myocardial infarctions begin to occur in heterozygous men in the third decade and peak in the fourth and fifth decades. By the age of sixty, approximately eighty-five percent of men have experienced a myocardial infarction. Women also experience an increased incidence of myocardial infarction, but the mean age of onset is ten years later.

FH homozygotes have two mutant alleles at the LDL receptor locus and are much more severely affected. These FH homozygotes have five- to sixfold elevations in plasma cholesterol levels. These individuals develop coronary, cerebral, and peripheral vascular atherosclerosis at an early age. FH homozygotes have marked elevations of LDL in the plasma from birth. Total cholesterol levels in homozygous FH are typically greater than 500 mg/dl (normal is 200 mg/dl), and the patients frequently have decreased high density lipoprotein levels. FH homozygotes typically succumb to complications from coronary heart disease prior to age 20, with males developing the disease earlier than females. Robbins, S. L. et al. (1984) Pathologic Basis of Disease (W.B. Saunders Company, Philadelphia) pp.139–140.

While drug therapy is available for FH heterozygotes, normal levels of plasma cholesterol are difficult to achieve. In the case of the FH homozygotes, the condition cannot be treated by conventional drug therapy, and the therapeutic recourses are limited to chronic plasmapheresis or orthotopic liver transplantation.

Whole liver transplantation, which is the current therapy for a variety of liver diseases, has been employed to successfully reconstitute LDL receptors in individuals with FH, thereby lowering serum cholesterol to normal levels. Whole liver transplantation, however, is limited by the scarcity of suitable donor organs. Li, Q. et al. (1993) Human Gene Therapy 4:403–409; Kay, M. A. et al. (1992) Proc. Natl. Acad. Sci. 89:89–93. In addition to the difficulty in obtaining donor organs, the expense of liver transplantation, estimated at approximately $200,000 to $300,000 per procedure, prohibits its widespread application. Another unsolved problem is graft rejection. Foreign livers and liver cells are poorly tolerated by the recipient and are rapidly destroyed by the immune system in the absence of immunosuppressive drugs. Li, Q. et al. (1993) Human Gene Therapy 4:403–409; Bumgardner, G. L. et al. (1992) Transplantation 53:857–862. While immunosuppressive drugs may be used to prevent rejection, they also block desirable immune responses such as those against bacterial and viral infections, thereby placing the recipient at risk of infection. There is a clear need, therefore, to address the limitations of the current liver transplantation therapy as treatment for the vast array of liver disorders.

SUMMARY OF THE INVENTION

To overcome the current limitations of whole liver transplantation to treat liver disorders, the present invention provides hepatocytes, compositions including the hepatocytes, and methods for treating disorders characterized by insufficient liver function by administering the hepatocytes to subjects with such disorders. The hepatocytes of the present invention offer several advantages over whole liver transplantation to treat liver disorders. For example, the hepatocytes of the present invention are isolated from pigs, which provide a convenient, relatively inexpensive, and abundant source of hepatocytes. Moreover, in some instances, the hepatocytes of the present invention are modified such that rejection of the hepatocytes upon introduction into a xenogeneic recipient is inhibited, thereby eliminating the requirement for generalized suppression of the immune system.

Accordingly, the present invention pertains to an isolated porcine hepatocyte or an isolated population of porcine hepatocytes suitable for transplantation into a xenogeneic subject, particularly a human subject. In a preferred embodiment, the xenogeneic subject has a disorder characterized by insufficient liver function. Examples of such disorders include hereditary disorders such as Gilbert's Syndrome, Crigler-Najjar Syndrome (either Type I or Type II), Dubin Johnson Syndrome, familial hypercholesterolemia, ornithine transcarbamoylase (OTC) deficiency, hereditary emphysema, and hemophilia; viral hepatitis, such as hepatitis A, B, and non-A, non-B hepatitis, hepatocellular carcinoma, acute liver failure, and chronic liver failure. The porcine hepatocyte(s), in unmodified form, has at least one antigen on the cell surface which is capable of stimulating an immune response against the cell in a xenogeneic subject, for example, a human. The antigen on the surface of the porcine hepatocyte is altered to inhibit rejection of the cell when introduced into a xenogeneic subject. In one embodiment, the cell surface antigen which is altered is an MHC class I antigen. This MHC class I antigen can be contacted, prior to transplantation into a xenogeneic subject, with at least one anti-MHC class I antibody, or a fragment or derivative thereof, which binds to the MHC class I antigen on the cell surface but does not activate complement or induce lysis of the cell. One example of an anti-MHC class I antibody is an anti-MHC class I F(ab')$_2$ fragment, such as an anti-MHC class I F(ab')$_2$ fragment of a monoclonal antibody PT85. The present invention also pertains to compositions which include porcine hepatocytes and antibodies, antibody fragments, or derivatives, which bind an antigen on the surface of the porcine hepatocytes. These compositions can be inserted into a delivery device, e.g., a syringe, e.g., a syringe pump, which facilitates the introduction of the cells into a subject. In addition, the porcine hepatocytes of the invention can be grown as a cell culture in a medium suitable to support the growth of the cells.

Porcine hepatocytes obtained from both embryonic (i.e., fetal), newborn, and adult pigs are suitable for transplantation into a xenogeneic subject. Typically, embryonic porcine hepatocytes are isolated during selected stages of gestational development. For example, hepatocytes can be isolated from an embryonic pig at a stage of embryonic development when the cells can be recognized as hepatocytes. In one embodiment, the hepatocytes are isolated between about day twenty (20) to about day twenty-five (25) of gestation and birth of the pig. In other preferred embodiments, the hepatocytes are isolated between about day thirty (30) to about day thirty-five (35) of gestation and birth of the pig, more preferably between about day twenty-five (25) and about day ninety (90) of gestation, still more preferably between about day thirty (30) and about day eighty (80) of gestation, yet more preferably between about day thirty-five (35) and about day seventy (70) of gestation, still further preferably between about day thirty-five (35) and about day fifty (50) to about day sixty (60) of gestation, and most preferably between about day thirty-five (35) and about day forty (40) of gestation.

The invention further pertains to an isolated porcine hepatocyte or an isolated population of hepatocytes isolated from a pig which is essentially free from organisms which are capable of transmitting infection or disease to a xenogeneic recipient, e.g., a human, of the cells. Categories of pathogens from which the pig are free can include parasites, bacteria, mycoplasma, and viruses. In one embodiment, the pig from which the hepatocytes are isolated is free of the following organisms: Toxoplasma, eperythrozoon, brucella, listeria, mycobacterium TB, leptospirillum, haemophilus suis, M. Hyopneumonia, porcine respiratory reproductive syndrome, rabies, pseudorabies, parvovirus, encephalomyocarditus virus, swine vesicular disease, techen (Porcine polio virus), hemagglutinating encephalomyocarditus, suipoxvirus, swine influenza type A, adenovirus, transmissible gastroenteritis virus, bovine viral diarrhea, and vesicular stomatitis virus. The cells obtained from pathogen-free pigs can be modified as described herein to inhibit rejection of the cell upon introduction into a xenogeneic subject. Preferred hepatocyte ages are described herein. The present invention also pertains to compositions which include porcine hepatocytes obtained from pathogen-free pigs and antibodies, antibody fragments, or derivatives, which bind an antigen on the surface of the porcine hepatocytes. These compositions can also be inserted into a delivery device, e.g., a syringe, e.g., a syringe pump, which facilitates the introduction of the cells into a subject.

Another aspect of the invention pertains to methods for treating disorders characterized by insufficient liver function, e.g., hereditary disorders such as Gilbert's Syndrome, Crigler-Najjar Syndrome (either Type I or Type II), Dubin Johnson Syndrome, familial hypercholesterolemia, OTC deficiency, hereditary emphysema and hemophilia; viral infections such as hepatitis A, B, and non-A, non-B hepatitis; hepatic malignancies such as hepatocellular carcinoma, acute liver failure, and chronic liver failure, in a subject, particularly a human subject. These methods include administering to a subject having such a disorder, an isolated population of porcine hepatocytes. In one embodiment, the porcine hepatocytes which can be administered to a subject having a liver disorder are porcine hepatocytes which, in unmodified form, have at least one antigen on the cell surface which is capable of stimulating an immune response against the cell in a xenogeneic subject, for example, a human. The antigen on the surface of the porcine hepatocyte is altered to inhibit rejection of the cell when introduced into a xenogeneic subject. Examples of hepatocyte cell surface antigens and methods of altering such antigens are described herein. Preferred hepatocyte ages are also described herein. In another embodiment, the porcine hepatocytes which can be administered to a subject having a disorder characterized by insufficient liver function are porcine hepatocytes which are obtained from a pig which is essentially free from organisms which are capable of transmitting infection or disease to a xenogeneic recipient, e.g., a human, of the cells. Pathogen-free pigs are described in detail herein. In one embodiment, administration of the porcine hepatocytes is accompanied by a step wherein the portal blood pressure is decreased, e.g., using an transjugular intra-hepatic porto-systemic shunt (TIPS). Transplantation of the porcine hepatocytes can be also accompanied by administration of an immunosuppressive agent, e.g., cyclosporine A, FK506, RS-61443, or a T cell antibody, to the subject.

BRIEF DESCRIPTION OF THE DRAWINGS

FIG. 3 is a graphic representation of total serum cholesterol levels in WHHL rabbits transplanted with porcine hepatocytes and treated with cyclosporin.

FIG. 4 is a graphic representation of the long term-effect of porcine hepatocyte transplantation in combination with cyclosporin treatment on total serum cholesterol in the WHHL rabbit.

FIG. 8 is a graphic representation of the lipoprotein profiles in the WHHL and New Zealand White rabbit transplanted with porcine hepatocytes and treated with cyclosporin as determined by FPLC.

FIG. 9 is a graphic representation of total serum cholesterol levels in WHHL rabbits transplanted with modified (i.e., masked) porcine hepatocytes.

FIG. 10 is a graphic representation of the effect of transplantation of masked porcine hepatocytes and administration of a subtherapeutic regimen of cyclosporin A on total serum cholesterol levels in WHHL rabbits.

FIG. 11 is a graphic representation of the clearance of $^{125}$I-hLDL from serum by a WHHL rabbit and a New Zealand White rabbit, neither of which was transplanted with porcine hepatocytes, and a WHHL rabbit transplanted with masked porcine hepatocytes.

FIG. 12 is a graphic representation of the lipoprotein profiles in the transplanted WHHL and New Zealand White rabbit transplanted with masked porcine hepatocytes as determined by FPLC.

DETAILED DESCRIPTION OF THE INVENTION

I. ISOLATED CELLS AND CELL POPULATIONS OF THE INVENTION

Figure 1:
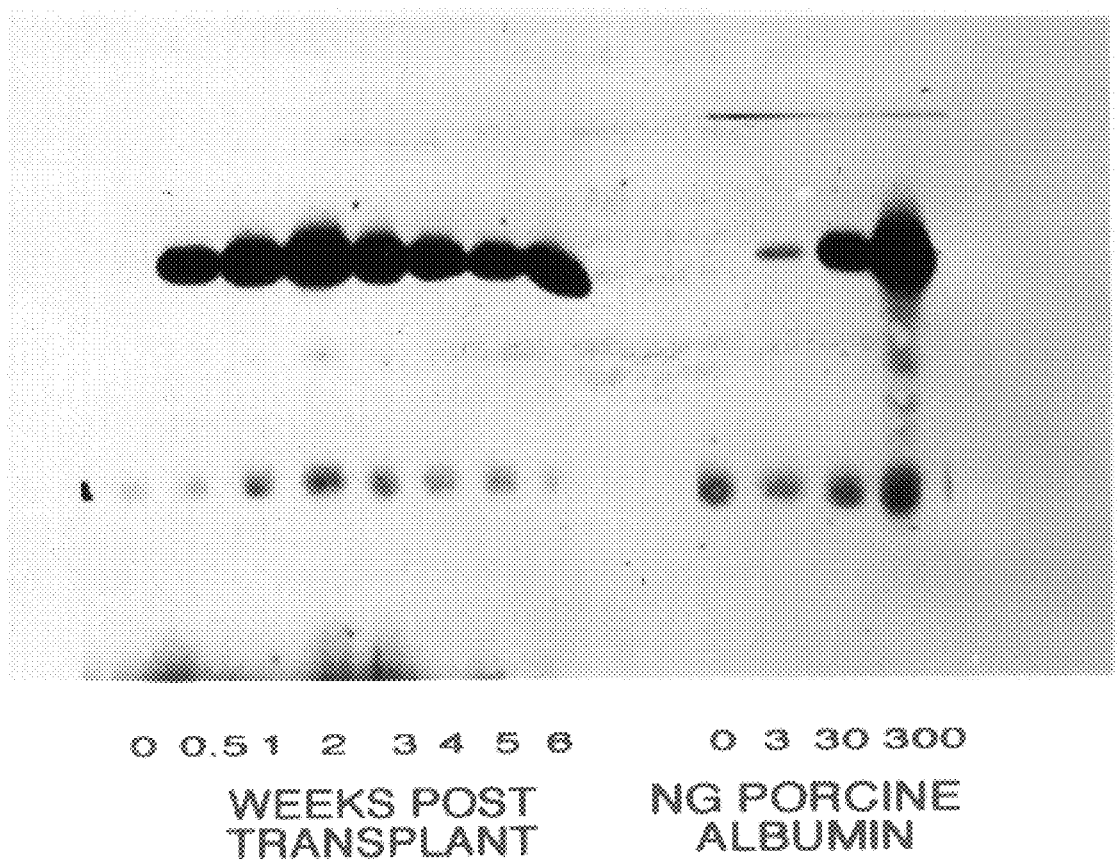
FIG. 1 is a Western blot showing porcine albumin production in a Watanabe heritable hyperlipidemic (WHHL) rabbit transplanted with porcine hepatocytes and treated with cyclosporin.

A. Porcine Hepatocytes Suitable for Administration to Xenogeneic Subjects

This invention features an isolated porcine hepatocyte and an isolated population of porcine hepatocytes which are suitable for administration to a xenogeneic subject. These cells can be used to treat disorders which are characterized by insufficient liver function. As used herein, the term "isolated" refers to a cell which has been separated from its natural environment. This term includes gross physical separation from its natural environment, e.g., removal from the donor animal, e.g., a pig, and alteration of the cell's relationship with the neighboring cells with which it is in direct contact by, for example, dissociation. The term "isolated" when used herein to refer to cell does not refer to a cell which is in a tissue section, is cultured as part of a tissue section, or is transplanted in the form of a tissue section. As used herein, the term "porcine" is used interchangeably with the terms "pig" and "swine" and refers to mammals in the family Suidae. Such mammals include wholly or partially inbred swine, e.g., miniature swine, and transgenic swine.

Hepatocytes are some of the most versatile cells in the body. Hepatocytes have both endocrine and exocrine functions, and synthesize and accumulate certain substance, detoxify others, and secrete others to perform enzymatic, transport, or hormonal activities. The main activities of liver cells include bile secretion, regulation of carbohydrate, lipid, and protein metabolism, storage of substances important in metabolism, degradation and secretion of hormones, and transformation and excretion of drugs and toxins. The term "hepatocyte" as used herein refers to a liver parenchymal cell.

Hepatocytes of the invention are obtained or isolated from the liver of a donor swine such as, for example, a swine which is essentially pathogen-free as described herein. Hepatocytes can be obtained or isolated from both adult, newborn (immature), and embryonic (i.e., fetal) swine. Embryonic hepatocytes are obtained from the liver of an embryonic donor swine and preferably at a selected gestational age. The selected gestational ages (the total gestation time for pig is approximately 115 days) for obtaining fetal or embryonic hepatocytes are determined based on the following criteria: the ability of the embryonic porcine liver structure to be identified; the viability of the cells upon isolation from the donor pig, the ability of the cells to proliferate in culture; the stage of development of the fetal liver is such that at least about 50% or more of the cells isolated therefrom are hepatocytes. The preferred gestational age of embryonic swine from which to obtain hepatocytes suitable for introduction into xenogeneic subjects, particularly humans, is between about day twenty (20) to about day twenty-five (25) of gestation and birth of the pig. Hepatocytes are preferably isolated between about day thirty (30) to about day thirty-five (35) of gestation and birth of the pig, more preferably between about day twenty-five (25) and about day ninety (90) of gestation, still more preferably between about day thirty (30) and about day eighty (80) of gestation, yet more preferably between about day thirty-five (35) and about day seventy (70) of gestation, still further preferably between about day thirty-five (35) and about day fifty (50) to about day sixty (60) of gestation, and most preferably between about day thirty-five (35) and about day forty (40) of gestation.

When isolated from a donor swine, the hepatocytes of the invention are capable of, among other functions, proliferating, secreting plasma proteins, such as albumin, expressing low density lipoprotein receptors and thus, binding low density lipoproteins, maintaining differentiated functions in vivo, and adhering to substrates, such as culture dishes. When isolated from a donor swine, the hepatocytes of the present invention also have an epithelial morphology and are binucleate.

The present invention also features a population of porcine hepatocytes. As used herein the term "population" refers to a group of two or more cells. The cells of the invention can be maintained as a functionally viable cell culture. The characteristics of the cells when grown as cell cultures are described herein in detail. Media which can be used to support the growth of porcine hepatocytes include mammalian cell culture media, such as those produced by Gibco BRL (Gaithersburg, Md.). See 1994 Gibco BRL Catalogue & Reference Guide. The medium can be serum-free but is preferably supplemented with animal serum such as fetal calf serum. A preferred medium is DMEM/Weymouths supplemented with fetal calf serum. When isolated from a donor pig and/or when maintained in culture, preferably at least about 20%, more preferably at least about 30%, yet more preferably at least about 40%, still more preferably at least about 50%, and most preferably at least about 60% or more of the hepatocytes express at least one liver-specific protein, e.g., albumin, LDL receptor.

The hepatocytes of the invention can be further included in compositions. For example, such compositions can include antibodies, antibody fragments, or derivatives, which bind to at least one antigen on the hepatocyte surface which is capable of stimulating an immune response against the hepatocyte in a xenogeneic subject. Hepatocyte surface antigens are described herein in detail. In one embodiment, the compositions can also include a pharmaceutically acceptable carrier or diluent as described herein.

Hepatocytes of the invention can also be "modified to express a gene product". As used herein, the term "modified to express a gene product" is intended to mean that the cell is treated in a manner that results in the production of a gene product by the cell. Preferably, the cell does not express the gene product prior to modification. Alternatively, modification of the cell can result in an increased production of a gene product already expressed by the cell or result in production of a gene product (e.g., an antisense RNA molecule) which decreases production of another, undesirable gene product normally expressed by the cell.

In a preferred embodiment, a cell is modified to express a gene product by introducing genetic material, such as a nucleic acid molecule (e.g., RNA or, more preferably, DNA) into the cell. The nucleic acid molecule introduced into the cell encodes a gene product to be expressed by the cell. The term "gene product" as used herein is intended to include proteins, peptides and functional RNA molecules. Generally, the gene product encoded by the nucleic acid molecule is the desired gene product to be supplied to a subject. Alternatively, the encoded gene product is one which induces the expression of the desired gene product by the cell (e.g., the introduced genetic material encodes a transcription factor which induces the transcription of the gene product to be supplied to the subject). Examples of gene products that can be delivered to a subject via a modified hepatocyte include low density lipoprotein receptors, blood clotting Factor VIII and Factor IX, UDP glucuronyl transferase, ornithine transcarbarroylase, and cytochrome p450 enzymes.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the gene product encoded by the gene. Regulatory sequences which can be included in the nucleic acid molecule include promoters, enhancers and polyadenylation signals, as well as sequences necessary for transport of an encoded protein or peptide, for example N-terminal signal sequences for transport of proteins or peptides to the surface of the cell or for secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements which are known in the art include upstream regions from the dystrophin gene (Klamut et al., (1989) *Mol. Cell. Biol.* 9:2396), the creatine kinase gene (Buskin and Hauschka, (1989) *Mol. Cell Biol*. 9:2627) and the troponin gene (Mar and Ordahl, (1988) *Proc. Natl. Acad Sci. USA*. 85:6404). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters). Alternatively, a regulatory element which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs. Alternatively, a regulatory element which provides inducible expression of a gene linked thereto can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S. and White, J. H. (1993) *Proc. Natl. Acad. Sci. USA* 90:5603–5607), synthetic ligand-regulated elements (see, e.g. Spencer, D. M. et al. (1993) *Science* 262:1019–1024) and ionizing radiation-regulated elements (e.g., see Manome, Y. et al. (1993) *Biochemistry* 32:10607–10613; Datta, R. et al. (1992) *Proc. Natl. Acad. Sci. USA* 89:10149–10153). Additional tissue-specific or inducible regulatory systems which may be developed can also be used in accordance with the invention.

There are a number of techniques known in the art for introducing genetic material into a cell that can be applied to modify a cell of the invention. In one embodiment, the nucleic acid is in the form of a naked nucleic acid molecule. In this situation, the nucleic acid molecule introduced into a cell to be modified consists only of the nucleic acid encoding the gene product and the necessary regulatory elements. Alternatively, the nucleic acid encoding the gene product (including the necessary regulatory elements) is contained within a plasmid vector. Examples of plasmid expression vectors include CDM8 (Seed, B., *Nature* 329:840 (1987)) and pMT2PC (Kaufman, et al., *EMBO J*. 6:187–195 (1987)). In another embodiment, the nucleic acid molecule to be introduced into a cell is contained within a viral vector. In this situation, the nucleic acid encoding the gene product is inserted into the viral genome (or a partial viral genome). The regulatory elements directing the expression of the gene product can be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells. or by incubating the cells and the DNA together in an appropriate buffer and subjecting the cells to a high-voltage electric pulse (i.e., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection. For cells in culture, DNA can be introduced by microinjection. For cells in vivo, DNA can be introduced through the use of a gene gun.

Alternatively, naked DNA can also be introduced into cells by complexing the DNA to a cation, such as polylysine, which is coupled to a ligand for a cell-surface receptor (see for example Wu, G. and Wu, C. H. (1988) *J. Biol. Chem*. 263:14621; Wilson et al. (1992) *J. Biol. Chem*. 267:963–967; and U.S. Pat. No. 5,166,320). Binding of the DNA-ligand complex to the receptor facilitates uptake of the DNA by receptor-mediated endocytosis. An alternative method for generating a cell that is modified to express a gene product involving introducing naked DNA into cells is to create a transgenic animal which contains cells modified to express the gene product of interest.

Use of viral vectors containing nucleic acid, e.g., a cDNA encoding a gene product, is a preferred approach for introducing nucleic acid into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for a review see Miller, A. D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques.

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells which efficiently express the gene product. Such a population of uniform cells can be prepared by isolating a single modified cell by limiting dilution cloning followed by expanding the single cell in culture into a clonal population of cells by standard techniques.

Alternative to introducing a nucleic acid molecule into a cell to modify the cell to express a gene product, a cell can be modified by inducing or increasing the level of expression of the gene product by a cell. For example, a cell may be capable of expressing a particular gene product but fails to do so without additional treatment of the cell. Similarly, the cell may express insufficient amounts of the gene product for the desired purpose. Thus, an agent which stimulates expression of a gene product can be used to induce or increase expression of a gene product by the cell. For example, cells can be contacted with an agent in vitro in a culture medium. The agent which stimulates expression of a gene product may function, for instance, by increasing transcription of the gene encoding the product, by increasing the rate of translation or stability (e.g., a post transcriptional modification such as a poly A tail) of an mRNA encoding the product or by increasing stability, transport or localization of the gene product. Examples of agents which can be used to induce expression of a gene product include cytokines and growth factors.

Another type of agent which can be used to induce or increase expression of a gene product by a cell is a transcription factor which upregulates transcription of the gene encoding the product. A transcription factor which upregulates the expression of a gene encoding a gene product of interest can be provided to a cell, for example, by introducing into the cell a nucleic acid molecule encoding the transcription factor. Thus, this approach represents an alternative type of nucleic acid molecule which can be introduced into the cell (for example by one of the previously discussed methods). In this case, the introduced nucleic acid does not directly encode the gene product of interest but rather causes production of the gene product by the cell indirectly by inducing expression of the gene product.

B. Modified Porcine Hepatocytes and Isolated Populations of Modified Porcine Hepatocytes A further aspect of the invention is a porcine hepatocyte (and an isolated population of porcine hepatocytes) which, in unmodified form, has at least one antigen on the cell surface which is capable of stimulating an immune response against the cell in a xenogeneic subject. To inhibit rejection of the cell when introduced into the xenogeneic subject, the antigen on the cell surface is altered prior to transplantation. In an unaltered state, the antigen on the cell surface stimulates an immune response against the cell when the cell is administered to a subject. By altering the antigen, the normal immunological recognition of the porcine hepatocyte by the immune system cells of the recipient is disrupted and additionally, "abnormal" immunological recognition of this altered form of the antigen can lead to porcine hepatocyte-specific long term unresponsiveness in the recipient. It is likely that alteration of an antigen on the porcine hepatocyte prior to introducing the cell into a subject interferes with the initial phase of recognition of the porcine hepatocyte by the cells of the host's immune system subsequent to administration of the cell. Furthermore, alteration of the antigen can induce immunological nonresponsiveness or tolerance, thereby preventing the induction of the effector phases of an immune response (e.g., cytotoxic T cell generation, antibody production etc.) which are ultimately responsible for rejection of foreign cells in a normal immune response. As used herein, the term "altered" encompasses changes that are made to at least one porcine hepatocyte antigen(s) which reduce the immunogenicity of the antigen to thereby interfere with immunological recognition of the antigen(s) by the recipient's immune system. An example of an alteration of a porcine hepatocyte antigen is binding of a second molecule to the antigen. The second molecule can decrease or prevent recognition of the antigen as a foreign antigen by the recipient subject's immune system.

Antigens to be altered according to the current invention include antigens on a hepatocyte which can interact with an immune cell in a xenogeneic (or allogeneic) recipient subject and thereby stimulate a specific immune response against the porcine hepatocyte in the recipient. The interaction between the antigen and the immune cell can be an indirect interaction (e.g., mediated by soluble factors which induce a response in the immune cell, e.g., humoral mediated) or, preferably, is a direct interaction between the antigen and a molecule present on the surface of the immune cell (i.e., cell-cell mediated). As used herein, the term "immune cell" is intended to include a cell which plays a role in specific immunity (e.g., is involved in an immune response) or plays a role in natural immunity. Examples of immune cells include-all distinct classes of lymphocytes (T lymphocytes, such as helper T cells and cytotoxic T cells, B lymphocytes, and natural killer cells), monocytes, macrophages, other antigen presenting cells, dendritic cells, and leukocytes (e.g., neutrophils, eosinophils, and basophils). In a preferred embodiment, the antigen is one which interacts with a T lymphocyte in the recipient (e.g., the antigen normally binds to a receptor on the surface of a T lymphocyte).

In one embodiment, the antigen on the porcine hepatocyte to be altered is an MHC class I antigen. Alternatively, an adhesion molecule on the cell surface, such as ICAM-1, can be altered. An antigen which stimulates a cellular immune response against the cell, such as an MHC class I antigen, can be altered prior to transplantation by contacting the cell with a molecule which binds to the antigen. A preferred molecule for binding to the antigen is an antibody, or fragment thereof (e.g., an MHC class I antibody, or fragment thereof). A preferred antibody fragment is an F(ab')$_2$ fragment. Polyclonal or, more preferably, monoclonal antibodies can be used. Other molecules which can be used to alter an antigen (e.g., an MHC class I antigen) include peptides and small organic molecules which bind to the antigen. Furthermore, two or more different epitopes on the same or different antigens on the cell surface can be altered. A particularly preferred monoclonal antibody for alteration of MHC class I antigens on porcine hepatocytes is PT85 (commercially available from Veterinary Medicine Research Development, Pullman Wash.). PT85 can be used alone to alter MHC class I antigens or, if each antibody is specific for a different epitope, PT85 can be used in combination with another antibody known to bind MHC class I antigens to alter the antigens on the cell surface. Suitable methods for altering a surface antigen on a cell for transplantation are described in greater detail in Faustman and Coe (1991) *Science* 252:1700–1702 and PCT publication WO 92/04033. Methods for altering multiple epitopes on a surface antigen on a cell for transplantation are described in greater detail in WO 95/26741, published on Oct. 12, 1995. The altered (also referred to herein as "modified") porcine cells can comprise an isolated population of cells. The characteristics of such populations are described above. The hepatocytes to be modified can be obtained from donor swine at the gestational ages described herein. Preferred donor swine are those which are essentially pathogen-free as described herein.

A preferred method for altering at least two different epitopes on an antigen on a donor cell to inhibit an immune response against the cell is to contact the cell with at least two different molecules which bind to the epitopes. It is preferred that the cell be contacted with at least two different molecules which bind to the different epitopes prior to administering the cell to a recipient (i.e., the cell is contacted with the molecule in vitro). For example, the cell can be incubated with the molecules which bind to the epitopes under conditions which allow binding of the molecules to the epitopes and then any unbound molecules can be removed (such as described in the Exemplification to follow). Following administration of the donor cell to a recipient, the molecules remain bound to the epitopes on the surface antigen for a sufficient time to interfere with immunological recognition by host cells and induce nonresponsiveness in the recipient.

Preferably, the molecule for altering an epitope on a donor cell is an antibody, or fragment or derivative thereof which retains the ability to bind to the epitope. For use in therapeutic applications, it is necessary that an antibody which binds the epitopes to be altered be unable to fix complement, thus preventing donor cell lysis., Antibody complement fixation can be prevented by deletion of an Fc portion of an antibody, by using an antibody isotype which is not capable of fixing complement, or, less preferably, by using a complement fixing antibody in conjunction with a drug which inhibits complement fixation. Alternatively, amino acid residues within the Fc region of an antibody which are important for activating complement (see e.g., Tan et al. (1990) *Proc. Natl. Acad. Sci. USA* 87:162–166; Duncan and Winter (1988) *Nature* 332: 738–740) can be mutated to reduce or eliminate the complement-activating ability of an intact antibody. Likewise, amino acids residues within the Fc region of an antibody which are necessary for binding of the Fc region to Fc receptors (see e.g. Canfield, S. M. and S. L. Morrison (1991) *J. Exp. Med.* 173:1483–1491; and Lund, J. et al. (1991) *J. Immunol.* 147:2657–2662) can also be mutated to reduce or eliminate Fc receptor binding if an intact antibody is to be used.

A preferred antibody fragment for altering an epitope is a F(ab')$_2$ fragment. Antibodies can be fragmented using conventional techniques. For example, the Fc portion of an antibody can be removed by treating an intact antibody with pepsin, thereby generating a F(ab')$_2$ fragment. In a standard procedure for generating F(ab')$_2$ fragments, intact antibodies are incubated with immobilized pepsin and the digested antibody mixture is applied to an immobilized protein A column. The free Fc portion binds to the column while the F(ab')$_2$ fragments passes through the column. The F(ab')$_2$ fragments can be further purified by HPLC or FPLC. F(ab')$_2$ fragments can be treated to reduce disulfide bridges to produce Fab' fragments.

An antibody, or fragment or derivative thereof, to be used to alter multiple epitopes on an antigen can be derived from polyclonal antisera containing antibodies reactive with a number of epitopes on the antigen. More preferably, however, two different epitopes on the same antigen are altered using two different monoclonal antibodies which bind to two different epitopes on the same antigen (e.g., an MHC class I antigen). Polyclonal and monoclonal antibodies which bind to different epitopes on one or more antigens can be prepared by standard techniques known in the art. For example, a mammal, (e.g., a mouse, hamster, or rabbit) can be immunized with an antigen (e.g., an MHC class I antigen) or with a cell which expresses the antigen (e.g., on the cell surface) to elicit an antibody response against the antigen in the mammal. Alternatively, tissue or a whole organ which expresses the antigen can be used to elicit antibodies. The progress of immunization can be monitored by detection of antibody titers in plasma or serum. Standard ELISA or other immunoassay can be used with the antigen to assess the levels of antibodies. Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these calls and yielding hybridoma cells. Such techniques are well known in the art. For example, the hybridoma technique originally developed by Kohler and Milstein ((1975) *Nature* 256:495–497) as well as other techniques such as the human B-cell hybridoma technique (Kozbar et al., (1983) *Immunol. Today* 4:72), and the EBV-hybridoma technique to produce human monoclonal antibodies (Cole et al. (1985) *Monoclonal Antibodies in Cancer Therapy*, Allen R. Bliss, Inc., pages 77–96) can be used. Hybridoma cells can be screened immunochemically for production of antibodies specifically reactive with the antigen and monoclonal antibodies isolated.

According to the invention, a cell for transplantation is treated prior to transplantation to alter, reduce or substantially eliminate expression of at least one epitope on the cell surface that stimulates hyperacute rejection of the cell in a recipient. In a preferred embodiment of the invention, expression of a surface epitope is reduced or substantially eliminated by removing the epitope from the cell surface. Removal of the natural antibody epitope from the cell surface inhibits subsequent recognition of the cell by natural antibodies in a transplant recipient. An epitope can be removed from the surface of a cell by treating the cell with an enzyme or chemical which cleaves the epitope from the surface of the cell. For example, carbohydrate epitopes can be cleaved from a cell surface by treatment of the cell with one or more endo- or exoglycosidases specific for the carbohydrate to be cleaved. Preferably, alpha-galactosyl epitopes are cleaved from a cell surface by treatment of the cell with an alpha-galactosidase. Treatment of cells in vitro prior to transplantation with an alpha-galactosidase (e.g., coffee bean alpha-galactosidase; commercially available from Sigma Chemical Co., St. Louis, Mo.) removes surface alpha-galactosyl epitopes. Following treatment, removal of these epitopes from the cell surface can be assessed, for example, by reacting the cells, with a labelled lectin specific for the alpha-galactosyl epitope (e.g., *Griffonia simplicifoia*, or GS-1, lectin; commercially available from EY Labs) and assessing the amount of binding of the labelled lectin to the treated cells compared to untreated control cells. It has been found that GS-1 binding activity on the surface of porcine endothelial cells is undetectable after alpha-galactosidase treatment. Moreover, it has been found that alpha-galactosyl epitopes on the cell surface are not reexpressed for several hours after treatment and that even 48 hours after treatment, GS-1 binding activity is still diminished by 60%. Thus, alpha-galactosidase treatment of cells is sufficient to remove surface alpha-galactosyl epitopes and this treatment leads to prolonged diminution of expression of these epitopes on the cell surface. In addition to alpha-galactosidase treatment, other carbohydrate moieties can be cleaved by a glycosidase having specificity for that moiety. Alternatively, a chemical treatment which removes one or more specific carbohydrate moieties, while retaining cell viability and function, can be used to remove natural antibody epitopes from the surface of a cell.

To remove cell-surface natural antibody epitopes, a cell is treated with an amount of enzyme (or chemical) and for a period of time sufficient to reduce or substantially eliminate expression of the epitope on the cell surface such that upon transplantation of the cell into a recipient hyperacute rejection of the cell is inhibited. Appropriate dosages and digestion times may vary depending, for example, upon the cell type being treated and the type of digestion reagent used. Appropriate digestion conditions can easily be determined by one skilled in the art according to the teachings of the invention. A non-limiting example of digestion conditions for removal of surface alpha-galactosyl epitopes is 500 milliunits of coffee bean alpha-galactosidase (Sigma Chemical Co., St. Louis, Mo.) per $1 \times 10^6$ cells for 2 hours at 37° C. in a buffer of 200 mM sodium acetate in phosphate buffered saline (PBS) (pH 5.8).

In another embodiment of the invention, expression of a cell surface natural antibody epitope is reduced or substantially eliminated by inhibiting or preventing formation of the epitope on the cell surface, e.g., by interfering with the synthesis of the epitope. For example, the activity of an enzyme within the cell which is necessary for formation of the epitope can be inhibited. Carbohydrate moieties are typically attached to glycoproteins or glycolipids by specific glycosyltransferases. Thus, expression of a carbohydrate epitope on a cell surface can be reduced or substantially eliminated by inhibiting the activity of a glycosyltransferase involved in the synthesis of the epitope. For example, the enzyme responsible for attaching galactose in alpha linkage to an underlying chain of sugars on both glycoproteins and glycolipids is UDP galactose alpha-1,3-galactosyltransferase (also referred to herein as alpha-galactosyltransferase). The enzyme substrate specificity and kinetics of this enzyme have been studied (see Elices, M. J. and Goldstein, I. J. (1989) *J. Biol. Chem.* 264:1375–1380; and Joziasse, D. H. et al. (1987) *J. Biol. Chem.* 262:2025–2033) and the gene for the enzyme has been cloned from bovine (Joziasse, D. H. et al. (1989) *J. Biol. Chem.* 264:14290–14297) and murine (Larsen, R. D. et al. (1989) *Proc. Natl. Acad. Sci. USA* 86:8227–8231) tissues. A gene is present in humans that displays considerable homology to the murine gene, but, due to a frameshift mutation and several nonsense mutations in the human counterpart of the murine gene (Larsen, R. D. et al. (1990) *J. Biol. Chem.* 265:7055–7061), the active enzyme is not synthesized in humans and Old World monkeys. As a result, this carbohydrate epitope which is recognized by the natural antibodies in human serum is not normally present on human cells.

In a preferred embodiment, the activity of a glycosyltransferase, e.g. an alpha-galactosyltransferase, is inhibited by introducing into a cell a nucleic acid which is antisense to a regulatory or coding region of the glycosyltransferase gene, thereby repressing transcription of the gene or translation of the mRNA. An "antisense" nucleic acid molecule comprises a nucleotide sequence which is complementary to a coding strand (i.e., sense strand) of another nucleic acid, e.g. complementary to an mRNA sequence, constructed according to the rules of Watson and Crick base pairing, and thus can hydrogen bond to the sense strand of the other nucleic acid. An antisense nucleic acid can form a duplex with an mRNA strand and prevent its efficient translation. Additionally, antisense nucleic acids may increase RNase-mediated degradation of mRNA and/or inhibit splicing of pre-mRNA. An antisense sequence can be complementary to a sequence found in the coding region of an mRNA or can be complementary to a 5' or 3' untranslated region of the mRNA. To inhibit translation, the antisense nucleic acid is preferably complementary to a region preceding or spanning the translation initiation codon. Alternatively, an antisense nucleic acid can bind to DNA to form a triple helix and prevent gene transcription (see e.g., Stein, C. A. and Cheng Y-C. (1993) *Science* 261:1004–1012). Thus, an antisense nucleic acid can be complementary in sequence to a regulatory region of a gene encoding a glycosyltransferase, for instance complementary to a transcription initiation sequence or regulatory element (e.g., promoter or enhancer sequence). For a discussion of the regulation of gene expression using antisense genes see Weintraub, H. et al., Antisense RNA as a molecular tool for genetic analysis, *Reviews—Trends in Genetics*, Vol. 1(1) 1986.

Epitopes on the surface of the hepatocytes, in one embodiment of the invention, are removed from the surface of a cell, such as by enzymatic or chemical treatment of the cell. For example, Gal($\alpha$1,3)Gal epitopes can be cleaved from a cell surface by treatment of the cell with an alpha-galactosidase. In another embodiment, formation of the epitope on the cell surface is inhibited. This can be accomplished by inhibiting the activity of an enzyme which forms the epitope. For example, formation of Gal($\alpha$1,3)Gal epitopes on the surface of a cell can be interfered with by inhibiting the activity of an alpha-1,3-galactosyltransferase within the cell, such as by introducing into the cell a nucleic acid which is antisense to a coding or regulatory region of an alpha-1,3-galactosyltransferase gene or by treating the cell with a chemical inhibitor of the enzyme. In yet another embodiment, epitopes on a hepatocyte surface are altered by binding a molecule to the epitope, thereby inhibiting its subsequent recognition by natural antibodies in a recipient. For example, lectins, antibodies or antibody fragments can be bound to an epitope to inhibit its subsequent recognition by natural antibodies. Methods for altering epitopes on cell surfaces which stimulate hyperacute rejection of the cells by natural antibodies in a recipient subject are described in greater detail in WO 95/33828, published on Dec. 14, 1995. Epitopes to be altered, reduced or substantially eliminated according to the invention are those which stimulate hyperacute rejection of a cell in a recipient. Since natural antibodies in humans and nonhuman primates are predominantly directed against carbohydrate epitopes, preferred epitopes for modification are carbohydrate moieties. A preferred carbohydrate epitope to be altered, reduced or substantially eliminated is a galactosyl($\alpha$1,3) galactose epitope (also referred to herein as Gal($\alpha$1,3)Gal or an alpha-galactosyl epitope). Up to 1% of all circulating IgG in human sera has been found to be directed against this epitope (see Galili, U. et al. (1987) *Proc. Natl. Acad. Sci. USA* 84:1369–1373; Galili, U. et al. (1987) *J. Biol Chem.* 262:4683–4688).

C. Porcine Hepatocytes and Isolated Populations of Porcine Hepatocytes Obtained from Essentially Pathogen-Free Swine The invention also features a porcine hepatocyte (and an isolated population of porcine hepatocytes) obtained from a swine which is essentially free from organisms or substances which are capable of transmitting infection or disease to a xenogeneic recipient, e.g., a human recipient, of the cells. Typically, porcine hepatocytes are obtained from a swine which is essentially free from pathogens which affect humans. For example, the pathogens from which the swine are free include, but are not limited to, one or more of pathogens from the following categories of pathogens: parasites, bacteria, mycoplasma, and viruses. The swine can be free from, for example, parasites such as toxoplasma and eperytherozoon, or mycoplasma, such as M. hyopneumonia. Examples of bacteria from which the swine can be free include brucella, listeria, mycobacterium TB, leptospirillum, and haemophilus suis. Additionally, the swine can be free from viruses such as zoonotic viruses (viruses which can be transferred from pigs to man under natural conditions), viruses that can cross the placenta in pregnant sows, and neurotropic viruses. Zoonotic viruses include, for example, a virus in the rabies virus group, a herpes-like virus which causes pseudorabies, encephalomyocarditus virus, swine influenza Type A, transmissible gastroenteritus virus, parainfluenza virus 3 and vesicular stomatitis virus. Viruses that can cross the placenta include, for example, viruses that cause porcine respiratory reproductive syndrome, a virus in the rabies virus group, a herpes-like virus which causes pseudorabies, parvovirus, a virus that causes swine vesicular disease, techen (porcine polio virus), hemmaglutinating encephalomyocarditus, cytomegalovirus, suipoxvirus, and swine influenza type A. Neurotropic viruses include, for example, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, adenovirus, parainfluenza 3 virus. Specific examples of viruses from which the swine are free include: a virus which causes (or results in) porcine respiratory reproductive syndrome, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, cytomegalovirus, suipoxvirus, swine influenza type A, adenovirus, transmissible gastroenteritus virus, a virus which causes bovine viral diarrhea, parainfluenza virus 3, and vesicular stomatitis virus.

In one embodiment, the pigs from which hepatocytes are isolated are essentially free from the following organisms: Toxoplasma, eperythrozoon, brucella, listeria, mycobacterium TB, leptospirillum, haemophilus suis, M. Hyopneumonia, a virus which causes porcine respiratory reproductive syndrome, a virus which causes rabies, a virus which causes pseudorabies, parvovirus, encephalomyocarditus virus, a virus which causes swine vesicular disease, porcine polio virus (techen), a virus which causes hemagglutinating encephalomyocarditus, suipoxvirus, swine influenza type A, adenovirus, transmissible gastroenteritis virus, a virus which causes bovine viral diarrhea, and vesicular stomatitis virus. The phrase "essentially free from organisms or substances which are capable of transmitting infection or disease to a xenogeneic recipient" (also referred to herein as "essentially pathogen-free") when referring to a swine from which cells are isolated means that that swine does not contain organisms or substances in an amount which transmits infection or disease to a xenogeneic recipient, e.g. a human. Example VII provides representative, but not limiting, examples of methods for selecting swine which are essentially free from various pathogens. The hepatocytes of the invention can be isolated from embryonic or post-natal swine which are determined to be essentially free of such organisms. These swine are maintained under suitable conditions until used as a source of hepatocytes.

Preferred gestational ages of the swine from which these cells are obtained are described in detail herein. Porcine hepatocytes obtained from essentially pathogen-free swine can additionally be modified to reduce the immunogenicity of the cells following administration to a xenogeneic subject as described herein.

II. METHODS OF THE INVENTION

A. Methods of Treating Disorders Characterized by Insufficient Liver Function Using Porcine Hepatocytes Still further aspects of the invention include methods for treating disorders characterized by insufficient liver function in a subject, particularly a human subject. These methods include administering to a xenogeneic subject, an isolated population of porcine hepatocytes described herein. The term "treating" as used herein includes reducing or alleviating at least one adverse effect or symptom of a disorder characterized by insufficient liver function. Non-limiting examples of adverse effects or symptoms of liver disorders include: high serum cholesterol and early onset atherosclerosis associated with familial hypercholesterolemia; absent glucuronyl transferase activity, impaired biliary excretion, severe unconjugated hyperbilirubinemia, and neurological damage associated with Crigler-Najjar Syndrome Type I; decreased glucuronyl transferase activity and unconjugated hyperbilirubinemia associated with Gilbert's Syndrome; cirrhosis and liver failure associated with chronic hepatitis or other causes such as alcohol abuse; death in infancy associated with OTC deficiency; alveolar tissue damage associated with hereditary emphysema; deficiency in clotting factor VIII associated with hemophilia A. For additional examples of adverse effects or symptoms of a wide variety of liver disorders, see Robbins, S. L. et al. (1984) Pathological Basis of Disease (W.B. Saunders Company, Philadelphia) 884–942. Transplantation of porcine hepatocytes of the invention into a subject with a liver disorder results in replacement of lost or damaged hepatocytes and replacement of liver function. Porcine hepatocytes are transplanted into a subject with a liver disorder in an amount suitable to replace lost or damaged hepatocytes such that there is an at least partial reduction or alleviation of at least one adverse effect or symptom of the liver disorder.

As used herein the terms "administering", "introducing", and "transplanting" are used interchangeably and refer to the placement of the porcine hepatocytes of the invention into a subject, e.g., a xenogeneic subject, by a method or route which results in localization of the hepatocytes at a desired site. The porcine hepatocytes can be administered to a subject by any appropriate route which results in delivery of the cells to a desired location in the subject where at least a portion of the cells remain viable. It is preferred that at least about 5%, preferably at least about 10%, more preferably at least about 20%, yet more preferably at least about 30%, still more preferably at least about 40%, and most preferably at least about 50% or more of the cells remain viable after administration into a subject. The period of viability of the cells after administration to a subject can be as short as a few hours, e.g., twenty-four hours, to a few days, to as long as a few weeks to months. Common methods of administering hepatocytes to subjects, particularly human subjects, include intraperitoneal injection of the cells, (Wilson, J. et al. (1991) *Clin. Biotech.* 3(1):21–25), intravenous infusion of the cells into, for example, the portal vein (Kay, M. (1993) *Cell Trans.* 2:405–406; Tejera, J. L. et al. (1992) *Transplan. Proc.* 24(1):160–161; Wiederkehr, J. C. et al. (1990) *Transplantation* 50(3):466–476), or the mesenteric vein (Grossman, M. et al. (1994) *Nature Gen.* 6:335–341; Wilson, J. M. et al. (1990) *Proc. Natl. Acad. Sci.* 87:8437–8441), intrasplenic injection of the cells (Rhim, J. A. et al. (1994) *Science* 263:1149–1152; Kay, M. A. (1993) *Cell Trans.* 2:405–406; Wiederkehr, J. C. et al. (1990) *Transplantation* 50(3): 466–476), and infusion of the cells into the splenic artery. To facilitate transplantation of the hepatocytes into, for example, the peritoneal cavity, the cells can be bound to microcarrier beads such as collagen-coated dextran beads (Pharmacia, Uppsala, Sweden) (Wilson, J. et al. (1991) *Clin. Biotech.* 3(1):21–25). Cells can be administered in a pharmaceutically acceptable carrier or diluent as described herein. A human liver typically consists of about $2\times10^{11}$ hepatocytes. To treat insufficient liver function in a human subject, about $10^9$–$10^{10}$ hepatocytes are transplanted into the subject. The whole liver of a pig weighing about fifty pounds yields about $10^{10}$ hepatocytes and provides, therefore, a sufficient number of hepatocytes for transplantation into a human subject.

To accomplish these methods of administration, the cells and/or compositions of the invention can be inserted into a delivery device which facilitates introduction of the cells and/or compositions into the subject. Such delivery devices include tubes, e.g., catheters, for infusing or injecting cells and fluids into the body of a recipient subject. In a preferred embodiment, the tubes additionally have a needle, e.g., a syringe, through which the cells of the invention can be introduced into the subject at a desired location. The porcine hepatocytes (and compositions containing the hepatocytes) of the invention can be inserted into such a delivery device, e.g., a syringe, e.g., syringe pump, in different forms. For example, the cells can be suspended in a solution or embedded in a support matrix when contained in such a delivery device. As used herein, the term "solution" includes a pharmaceutically acceptable carrier or diluent in which the cells of the invention remain viable. Pharmaceutically acceptable carriers and diluents include sterile saline and aqueous buffer solutions. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating porcine hepatocytes as described herein in a pharmaceutically acceptable carrier or diluent and, as required, other ingredients enumerated above, followed by filtered sterilization.

Support matrices in which the porcine hepatocytes can be incorporated or embedded include matrices which are recipient-compatible and which degrade into products which are not harmful to the recipient. Natural and/or synthetic biodegradable matrices are examples of such matrices. Natural biodegradable matrices include collagen matrices. Synthetic biodegradable matrices include synthetic polymers such as polyanhydrides, polyorthoesters, and polylactic acid. These matrices provide support and protection for the hepatocytes in vivo.

Administration of the porcine hepatocytes of the invention to a subject can be accompanied by a step which involves decreasing portal blood pressure. The livers of subjects suffering from disorders characterized by insufficient liver function, e.g., chronic liver disease, become fibrotic and form nodules. Depending on the etiology of the disorder, there is a variable component of hepatocyte necrosis. As hepatocyte function is lost, liver failure becomes clinically apparent when only 10% of liver cells are functioning. Sinusoidal compression and scarring lead to portal hypertension and eventually its complications which include variceal bleeding, ascites and encephalopathy. Thus, as subjects treated according to the present invention will, in most cases, be experiencing suboptimal or insufficient liver function accompanied by portal hypertension, it is desirable to minimize increases in portal blood pressure upon transplantation of the porcine hepatocytes of the invention. Thus, methods of the invention can include the step of decreasing or maintaining portal blood pressure of the subject receiving the porcine hepatocyte transplant. As used herein, a "decrease in portal blood pressure" of a subject refers to a blood pressure level in a subject which decreases after transplantation of the porcine hepatocytes of the invention relative to the portal blood pressure level of the subject prior to transplantation of the porcine hepatocytes of the invention. Similarly, as used herein, the phrase "maintaining portal blood pressure" refers to a blood pressure level in a subject which remains about the same, e.g., is stable, before and after transplantation of the porcine hepatocytes of the invention.

In one embodiment, the portal blood pressure of a subject is decreased or maintained through the use of an transjugular intra-hepatic porto-systemic shunt (TIPS). See e.g., Rossle, M. and Ring, E. J. in Progress in Liver Disease (Saunders, 1994) Vol. XII:177–189; Ochs, A. et al. (1995) N. Engl. J. Med. 332(18):1192–1196; Rossle, M. et al. (1994) N. Engl. J. Med. 330(3):165–171. At present, TIPS is used alone to relieve various symptoms, e.g. complications of portal hypertension such as variceal hemorrhage, related to liver disease but does not improve the prognosis of the subject receiving the TIPS. TIPS, when used in combination with the method of treating a subject by administering to the subject the porcine hepatocytes of the invention, relieves the symptoms of the liver disease or disorder and improves the prognosis of the subject. The porcine hepatocytes administered to the subject with the liver disease or disorder repopulate the liver and provide liver function to the subject.

The TIPS procedure includes the passage of a tube e.g., needle, catheter, which acts as a shunt, from the jugular vein into a hepatic vein and then advancing the tube through the liver parenchyma into a portal vein branch. This shunt allows blood flowing through the portal venous system to pass directly from the portal vein into the hepatic vein, thereby bypassing the liver parenchyma. Bypass of the liver parenchyma results in a decrease or at least a maintenance of the portal blood pressure in a subject after transplantation of the porcine hepatocytes of the invention. The step of decreasing or maintaining the portal venous blood pressure in a subject can be performed prior to, during, or after transplantation of the porcine hepatocytes of the invention. Preferably, the hepatocytes of the invention are administered to the subject via the TIPS catheter into the portal vein, thereby eliminating the need for providing an additional route of administration for the hepatocytes. In a preferred embodiment, the step of decreasing or maintaining the portal venous blood pressure in a subject is performed after transplantation of the porcine hepatocytes of the invention. Typically, hepatocytes of the invention are transplanted and the portal blood pressure is decreased or maintained by performance of the following steps: 1) transjugular cannulation of the portal vein; 2) transplantation of hepatocytes into the liver via the portal vein, e.g., through the use of the cannula in the portal vein; and 3) placement of the TIPS within the liver.

The term "subject" as used herein refers to mammals, particularly humans, susceptible to disorders characterized by insufficient liver function. The term "subject" also includes mammals in which an immune response is elicited against allogeneic or xenogeneic cells. Examples of subjects include primates (e.g., humans, and monkeys). A "xenogeneic subject" (also referred to herein as "recipient subject" or "recipient") as used herein is a subject into which cells of another species are introduced or are to be introduced.

As used herein, the language "disorder characterized by insufficient liver function" includes a disorder in which there is abnormal liver function. Abnormal liver function includes an impairment or absence of a normal liver function or presence of an abnormal liver function. Abnormal liver function can result from a genetic disorder involving, for example, a cell surface protein. An example of such a disorder is familial hypercholesterolemia which is characterized by a low expression of the low density lipoprotein receptor. Abnormal liver function can also result from a genetic disorder involving a liver enzyme. Examples of genetic disorders involving a liver enzyme include Crigler-Najjar Syndrome Type I and Type II, OTC deficiency, and phenylketonuria. In Crigler-Najjar Syndrome Type I, infants lack the enzyme UDP-glucuronyl transferase which is necessary to conjugate and excrete bilirubin, the breakdown product of heme from red blood cells. The toxic metabolites that accumulate as a result of this Syndrome cause fatal neurological damage. OTC deficiency is caused by a lack of the urea cycle enzyme, ornithine transcarbamoylase. This deficiency results in death in infancy. Phenylketonuria results from a lack of the liver enzyme phenylalanine hydroxylase. If untreated, lack of phenylalanine hydroxylase leads to hyperphenylalaninemia and usually mental retardation.

Alternatively, abnormal liver function can result from a genetic disorder involving secreted proteins. Hereditary emphysema, for example, is a genetic disorder occurring in one in 2,000 individuals in which there is a mutation in a secreted protein, alpha-1-antitrypsin (AAT). In the absence of functional AAT, neutrophil elastase, released during lung inflammation, proceeds unopposed to damage alveolar tissue. Hemophilias are bleeding disorders resulting from genetic defects in several of the clotting factors that are secreted by the liver. Hemophilia A, for example, is caused by a deficiency in Factor VIII, a clotting factor secreted by hepatocytes. These genetic disorders all result from the inability of the liver to produce (and, in some instances) secrete various proteins which it normally produces or to produce various proteins at the level which they are normally produced.

Abnormal liver function can result from a variety of non-genetic disorders that cause acute liver failure or that lead to chronic liver failure. Acute liver failure can result from a number of different causes such as drug or toxin ingestion, viral infection, and metabolic disease. Drugs which have been associated with acute liver failure include halothane, isoniazid, α-methyldopa, acetaminophen, and iproniazid. Viral infection, such as by hepatitis A virus, hepatitis B virus, or the group non-A, non-B hepatitis viruses, can also be a cause of acute liver failure. Chronic liver failure is most often caused by alcoholic cirrhosis and chronic active hepatitis. Hepatitis B and the non-A, non-B hepatitis viruses are the viruses most often associated with chronic liver failure. The methods of the invention can result in alleviation or reduction of any one or a combination of the adverse effects or symptoms of liver disorders described herein and/or which are known in the art.

Prior to introduction into a subject, the porcine hepatocytes can be modified to inhibit immunological rejection. The porcine hepatocytes can, as described in detail herein, be rendered suitable for introduction into a xenogeneic subject by alteration of at least one immunogenic cell surface antigen (e.g., an MHC class I antigen). To inhibit rejection of transplanted porcine hepatocytes and to achieve immunological non-responsiveness in an allogeneic or xenogeneic transplant recipient, the method of the invention can include alteration of immunogenic antigens on the surface of the porcine hepatocytes prior to introduction into the subject. This step of altering one or more immunogenic antigens on porcine hepatocytes can be performed alone or in combination with administering to the subject an agent which inhibits T cell activity in the subject. Alternatively, inhibition of rejection of a porcine hepatocyte graft can be accomplished by administering to the subject an agent which inhibits T cell activity in the subject in the absence of prior alteration of an immunogenic antigen on the surface of the porcine cardiomyocytes. As used herein, an agent which inhibits T cell activity is defined as an agent which results in removal (e.g., sequestration) or destruction of T cells within a subject or inhibits T cell functions within the subject (i.e., T cells may still be present in the subject but are in a non-functional state, such that they are unable to proliferate or elicit or perform effector functions, e.g. cytokine production, cytotoxicity etc.). The term "T cell" encompasses mature peripheral blood T lymphocytes. The agent which inhibits T cell activity may also inhibit the activity or maturation of immature T cells (e.g., thymocytes).

A preferred agent for use in inhibiting T cell activity in a recipient subject is an immunosuppressive drug. The term "immunosuppressive drug or agent" is intended to include pharmaceutical agents which inhibit or interfere with normal immune function. A preferred immunsuppressive drug is cyclosporin A. Other immunosuppressive drugs which can be used include FK506, RS-61443, and deoxyspergualin. In one embodiment, the immunosuppressive drug is administered in conjunction with at least one other therapeutic agent. Additional therapeutic agents which can be administered include steroids (e.g., glucocorticoids such as prednisone, methyl prednisolone and dexamethasone) and chemotherapeutic agents (e.g., azathioprine and cyclosphosphamide). In another embodiment, an immunosuppressive drug is administered in conjunction with both a steroid and a chemotherapeutic agent. Suitable immunosuppressive drugs are commercially available (e.g., cyclosporin A is available from Sandoz, Corp., East Hanover, N.J.).

An immunosuppressive drug is administered in a formulation which is compatible with the route of administration. Suitable routes of administration include intravenous injection (either as a single infusion, multiple infusions or as an intravenous drip over time), intraperitoneal injection, intramuscular injection and oral administration. For intravenous injection, the drug can be dissolved in a physiologically acceptable carrier or diluent (e.g., a buffered saline solution) which is sterile and allows for syringability. Dispersions of drugs can also be prepared in glycerol, liquid polyethylene glycols, and mixtures thereof and in oils. Convenient routes of administration and carriers for immunsuppressive drugs are known in the art. For example, cyclosporin A can be administered intravenously in a saline solution, or orally, intraperitoneally or intramuscularly in olive oil or other suitable carrier or diluent.

An immunosuppressive drug is administered to a recipient subject at a dosage sufficient to achieve the desired therapeutic effect (e.g., inhibition of rejection of transplanted cells). Dosage ranges for immunosuppressive drugs, and other agents which can be coadministered therewith (e.g., steroids and chemotherapeutic agents), are known in the art (See e.g., Freed et al. *New Engl. J. Med.* (1992) 327:1549: Spencer et al. (1992) *New Engl. J. Med.* 327:1541; Widner et al. (1992) *New Engl. J. Med.* 327:1556; Lindvall et al. (1992) *Ann. Neurol.* 31:155; and Lindvall et al. (1992) *Arch. Neurol.* 46:615). A preferred dosage range for immunosuppressive drugs, suitable for treatment of humans, is about 1–30 mg/kg of body weight per day. A preferred dosage range for cyclosporin A is about 1–10 mg/kg of body weight per day, more preferably about 1–5 mg/kg of body weight per day. Dosages can be adjusted to maintain an optimal level of the immunosuppressive drug in the serum of the recipient subject. For example, dosages can be adjusted to maintain a preferred serum level for cyclosporin A in a human subject of about 100–200 ng/ml. It is to be noted that dosage values may vary according to factors such as the disease state, age, sex, and weight of the individual. Dosage regimens may be adjusted over time to provide the optimum therapeutic response according to the individual need and the professional judgment of the person administering or supervising the administration of the compositions, and that the dosage ranges set forth herein are exemplary only and are not intended to limit the scope or practice of the claimed composition.

In one embodiment of the invention, an immunosuppressive drug is administered to a subject transiently for a sufficient time to induce tolerance to the transplanted cells in the subject. Transient administration of an immunosuppressive drug has been found to induce long-term graft-specific tolerance in a graft recipient (See Brunson et al. (1991) *Transplantation* 52:545; Hutchinson et al. (1981) *Transplantation* 32:210; Green et al. (1979) *Lancet* 2:123; Hall et al. (1985) *J. Exp. Med.* 162:1683). Administration of the drug to the subject can begin prior to transplantation of the cells into the subject. For example, initiation of drug administration can be a few days (e.g., one to three days) before transplantation. Alternatively, drug administration can begin the day of transplantation or a few days (generally not more than three days) after transplantation. Administration of the drug is continued for sufficient time to induce donor cell-specific tolerance in the recipient such that donor cells will continue to be accepted by the recipient when drug administration ceases. For example, the drug can be administered for as short as three days or as long as three months following transplantation. Typically, the drug is administered for at least one week but not more than one month following transplantation. Induction of tolerance to the transplanted cells in a subject is indicated by the continued acceptance of the transplanted cells after administration of the immunosuppressive drug has ceased. Acceptance of transplanted tissue can be determined morphologically (e.g., with biopsies of liver) or by assessment of the functional activity of the graft.

Another type of agent which can be used to inhibit T cell activity in a subject is an antibody, or fragment or derivative thereof, which depletes or sequesters T cells in a recipient. Antibodies which are capable of depleting or sequestering T cells in vivo when administered to a subject are known in the art. Typically, these antibodies bind to an antigen on the surface of a T cell. Polyclonal antisera can be used, for example anti-lymphocyte serum. Alternatively, one or more monoclonal antibodies can be used. Preferred T cell-depleting antibodies include monoclonal antibodies which bind to CD2, CD3, CD4 or CD8 on the surface of T cells. Antibodies which bind to these antigens are known in the art and are commercially available (e.g., from American Type Culture Collection). A preferred monoclonal antibody for binding to CD3 on human T cells is OKT3 (ATCC CRL 8001). The binding of an antibody to surface antigens on a T cell can facilitate sequestration of T cells in a subject and/or destruction of T cells in a subject by endogenous mechanisms. Alternatively, a T cell-depleting antibody which binds to an antigen on a T cell surface can be conjugated to a toxin (e.g., ricin) or other cytotoxic molecule (e.g., a radioactive isotope) to facilitate destruction of T cells upon binding of the antibody to the T cells. See WO 95/26740, published on Oct. 12, 1995, for further details concerning the generation of antibodies which can be used in the present invention.

Another type of antibody which can be used to inhibit T cell activity in a recipient subject is an antibody which inhibits T cell proliferation. For example, an antibody directed against a T cell growth factor, such as IL-2, or a T cell growth factor receptor, such as the IL-2 receptor, can inhibit proliferation of T cells (See e.g., DeSilva, D. R. et al. (1991) *J. Immunol.* 147:3261–3267). Accordingly, an IL-2 or an IL-2 receptor antibody can be administered to a recipient to inhibit rejection of a transplanted cell (see e.g. Wood et al. (1992) *Neuroscience* 49:410). Additionally, both an IL-2 and an IL-2 receptor antibody can be coadministered to inhibit T cell activity or can be administered with another antibody (e.g., which binds to a surface antigen on T cells).

An antibody which depletes, sequesters or inhibits T cells within a recipient can be administered at a dose and for an appropriate time to inhibit rejection of cells upon transplantation. Antibodies are preferably administered intravenously in a pharmaceutically acceptable carrier or diluent (e.g., a sterile saline solution). Antibody administration can begin prior to transplantation (e.g., one to five days prior to transplantation) and can continue on a daily basis after transplantation to achieve the desired effect (e.g., up to fourteen days after transplantation). A preferred dosage range for administration of an antibody to a human subject is about 0.1–0.3 mg/kg of body weight per day. Alternatively, a single high dose of antibody (e.g., a bolus at a dosage of about 10 mg/kg of body weight) can be administered to a human subject on the day of introduction of the hepatocytes into the subject. The effectiveness of antibody treatment in depleting T cells from the peripheral blood can be determined by comparing T cell counts in blood samples taken from the subject before and after antibody treatment. Dosage regimes can be adjusted over time to provide the optimum therapeutic response according to the individual need and the professional judgment of the person administering or supervising the administration of the compositions. Dosage ranges set forth herein are exemplary only and are not intended to limit the scope or practice of the claimed composition.

To assess their therapeutic potential in humans, the porcine hepatocytes of the invention can be introduced into existing animal models for, for example, familial hypercholesterolemia, Crigler-Najjar Syndrome Type I, OTC deficiency, and acute liver failure. The Watanabe heritable hyperlipidemic (WHHL) rabbit, an animal model for homozygous familial hypercholesterolemia, has a mutation in the low density lipoprotein (LDL) receptor that results in defective clearance of LDL and accumulation of cholesterol-rich lipoproteins in plasma. Brown, M. S. et al. (1986) *Science* 232:34–47; Havel, R. J. et al. (1989) *Arteriosclerosis Supplement* 9:I-33-I-38; Yamamoto, T. et al. (1986) *Science* 232:1230–1237. In addition, the Gunn rat, which lacks the enzyme UDP-glucuronyl transferase, which is necessary to conjugate and excrete bilirubin, the breakdown product of heme from red blood cells, is an animal model of Crigler-Najjar Syndrome Type I. Dixit, W. et al. (1993) *Transplantation* 55:616–622. Toxic metabolites that accumulate in the absence of this enzyme can cause fatal neurological damage. A mouse model of OTC deficiency is also available. Morsy, M. A. et al. (1993) *J. Clin. Invest.* 92:1580–1586. Treatment of mice and rats with the selective hepatotoxin, D-galactosamine, results in necrosis of the hepatic parenchyma and death due to acute liver failure. This model of acute liver failure is described in Shinozuka, H. et al. (1973) *Fed. Proc.* 32:1516–1526. Other animal models, e.g., rat and dog, of cirrhosis are available to assess the therapeutic potential of porcine hepatocytes in humans. These models are described further herein.

The therapeutic efficacy of the administered porcine hepatocytes in the WHHL rabbit is typically determined by, for example, measurement of serum cholesterol levels and clearance of radioactive LDL as described in the Examples section. Normalization of serum hypercholesterolemia demonstrates that the administered porcine hepatocytes can be used to treat familial hypercholesterolemia. The efficacy of the administered porcine hepatocyes in the Gunn rat is measured by total serum bilirubin levels or conjugated bilirubin levels. The efficacy of the administered porcine hepatocytes in the OTC-deficient mouse model can be measured by increased levels of OTC as described, for example, in Grompe, M. et al. (1992) *Hum. Gene Therapy* 3:35. Other methods of determining the therapeutic potential are histological examination of the hepatocyte graft (via a biopsy), e.g., by staining for, for example, the presence of an enzyme not produced in the recipient subject but provided by the administered porcine hepatocytes. In the case of acute hepatic failure, hepatocyte transplantation is especially suited for short term provision of, for example, metabolic function in a subject waiting for a whole liver transplant or in a subject with acute liver damage, e.g., caused by viral hepatitis, while the subject's liver is regenerating after removal of the damage-causing agent. Chronic liver failure induced by, for example, carbon tetrachloride, can also be treated by hepatocyte transplantation.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example I

Isolation of Porcine Hepatocytes

Male Yorkshire outbred pigs (20–30 kg) were obtained from the Tufts Veterinary Facility in Grafton, Mass. The pigs were sacrificed and the left lateral lobe was mobilized, clamped and excised. The lobe was perfused with cold PBS (1 liter). A second perfusion (500 ml) with ViaSpan (Belzer UW) (Dupont, Wilmington, Del.) was performed prior to transport to from Tufts Veterinary Facility to the transplant facilities. Liver lobes were transported on ice in ViaSpan.

Porcine hepatocytes were isolated by the two stage perfusion technique originally described by Berry and Friend ((1969) *J. Cell Biol.* 43:506–520) and modified by others (Maganto P. et al. (1992) *Transplant Proc.* 24:2826–2827; Gerlach J. C. et al. (1994) *Transplantation* 57:1318–1322) for ex vivo perfusion of large animal organs. A liver lobe of 100–200 g was cannulated and perfused with HBSS (minus $Mg^{++}$, $Ca^{++}$) containing 0.4 mM EDTA, 10 mM HEPES, pH 7.4 and penicillin (100 U/ml)-streptomycin (100 ug/ml) at 35° C. This was followed by a second perfusion with complete HBSS containing collagenase P (0.8 mg/ml, Boehringer Mannheim), 10 mM HEPES, pH 7.4, and penicillin-streptomycin at 35° C. The perfusion was continued until visible softening of the organ had occurred. The total time for digestion ranged from 12–20 minutes. The digested liver was then physically disrupted and the released hepatocytes were washed (50×g) twice in DMEM/Weymouth media containing 10% heat inactivated calf serum at 4° C.

Porcine hepatocytes were collected and counted. Viability was assessed by trypan blue staining and was routinely greater than 88%. Mean cell yields were $2.1+/-1\times10^7$/gram wet weight. The purity of the hepatocyte preparation was judged to be over 98% by immunofluorescence for class II bearing non-parenchymal cells. Purity determinations were made by counting the positive staining cells (monoclonal antibody ISCR3) in several fields consisting of 200 cells. Cells were stored in cold (4° C.) HBSS or ViaSpan transport medium up to 5 hours prior to transplantation. Immediately prior to infusion the hepatocytes were centrifuged at 50×g for 5 minutes. The hepatocytes were gently resuspended in 20 ml HBSS containing penicillin/streptomycin or gentamycin and 10 units/ml heparin at $1\times10^7$ cells/ml.

Example II

Transplantation of Porcine Hepatocytes into Watanabe Heritable Hyperlipidemic Rabbits and Demonstration of Hepatocyte Survival In Vivo The Watanabe heritable hyperlipidemic (WHHL) rabbit, an animal model for homozygous familial hypercholesterolemia (FH), has a mutation in the low density lipoprotein (LDL) receptor that results in defective clearance of LDL and accumulation of cholesterol-rich lipoproteins in plasma. WHHL rabbits were purchased from CAMM Research (Wayne, N.J.). The rabbits received standard rabbit chow and water ad libitum. WHHL rabbits (2–3 kg) were anesthetized with xylazine and ketamine and maintained under isoflurane. An incision distal and parallel to the end of the rib cage was made. The peritoneum was incised and the portal vein exposed. Hepatocytes ($2\times10^8$) suspended in 20 ml of HBSS (20° C.) were infused into the portal vein via a 25 gauge syringe connected to a Baxter model A infusion pump at approximately 1 ml/min. Portal hypertension was not monitored, but higher infusion rates resulted in significant mortality presumably due to portal occlusion. The injection site was covered with gel foam to prevent leakage as needed. Using this protocol, surgical mortality was minimized (below 13%). Cyclosporin A (Sandimmune, Sandoz) was administered daily at 10 mg/kg (s.c.) starting on the day of surgery.

The serum from WHHL rabbits was subjected to immunoprecipitation using an anti-porcine albumin antibody (Research Plus, Bayonne, N.J.) coupled to CNBr activated Sepharose 4B (Pharmacia). To eliminate cross reactivity with rabbit albumin the anti-porcine albumin antiserum was preabsorbed over an affinity column prepared by coupling rabbit albumin to CNBr Sepharose 4B. Serum samples (50 µl) were diluted in PBS containing 0.2% Tween-20 to a total reaction volume of 250 µl. Samples were incubated for 20 hours at 4° C. with gentle rocking. Beads were centrifuged and washed in PBS-Tween-20 prior to final resuspension in gel loading buffer. Samples were run on 8% SDS-polyacrylamide gels. Gels were electophoretically transferred to nitrocellulose and probed with a goat anti-porcine albumin antibody (Bethyl Laboratories, Montgomery, Tex.). The immunoblots were incubated with horseradish peroxidase conjugated anti-goat IgG . The immune complexes were visualized by ECL (Amersham Life Sciences). Pretransplant bleeds and commercial porcine albumin were used as controls. The antibody used does not detect rabbit serum albumin as shown in the Western blot of the pretransplant serum. The results of this experiment are illustrated in FIG. 1. The production of porcine albumin confirmed the presence of viable functioning hepatocytes in the graft. Serum samples indicated the presence of porcine albumin 6 weeks after transplantation, the last time point assayed.

To assess the secretion of porcine albumin in all the rabbits, a capture ELISA was developed for porcine albumin. The capture ELISA was developed using the rabbit (Research Plus) anti-porcine albumin antibody coated on 96 well microtiter plates. Rabbit serum (1:10 diluted) was added to the plate and after washing and binding of the goat anti-porcine albumin antibody (Bethyl Laboratories), detection was carried out with horseradish peroxidase conjugated anti-goat IgG (Jackson ImmunoResearch, West Grove, Pa.) and o-phenylenediamine. The sensitivity of this assay was in the nanogram range. Porcine albumin was assayed in animals at 2 weeks and 1 month post surgery. The results are shown in Table I. Rabbit serum was collected at the times indicated and analyzed using the capture assay. All transplanted animals showed albumin production in the µg/ml range with the exception of R3728. Sham surgery animals (R3535) were consistently negative for porcine albumin production.

TABLE 1

| Rabbit ID Number | Porcine Albumin ($A_{490}$) at Seven Days Post-Transplant | Porcine Albumin ($A_{490}$) at Thirty Days Post-Transplant |
| --- | --- | --- |
| Transplanted Rabbits | | |
| R3530[1] | 1.08 | 0.48 |
| R3533 | 0.98 | 0.66 |
| R3736 | 1.33 | 0.64 |
| R3738 | 0.81 | 0.54 |
| R4045 | 0.91 | 0.09 |
| R3744 | 0.15 | 0.04 |
| R3745 | 0.21 | 0.07 |
| Control Rabbit | | |
| R3739[2] | 0.00 | 0.00 |

[1]All animals received cyclosporin at 10 mg/kg/day. One animal (R3728) did not exhibit detectable porcine albumin in this assay.
[2]Sham surgery control.

Figure 2A:
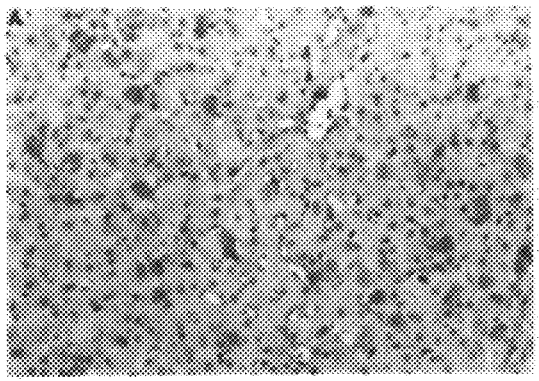
FIGS. 2A–2F show localization of porcine albumin in liver sections of the WHHL rabbit transplanted with porcine hepatocytes and treated with cyclosporin.
Figure 2B:
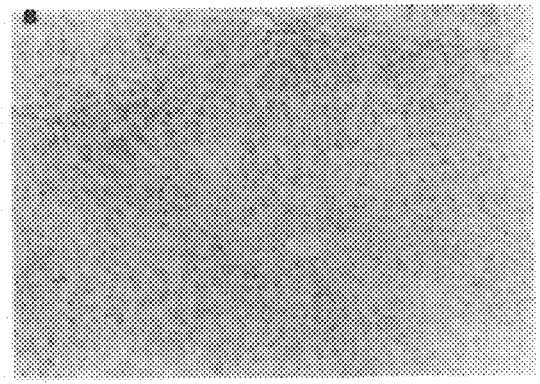
Figure 2C:
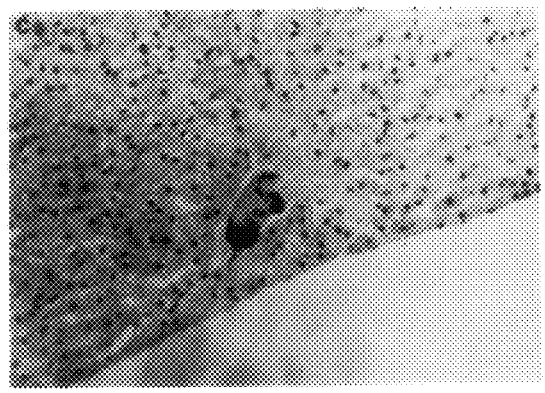
Figure 2D:
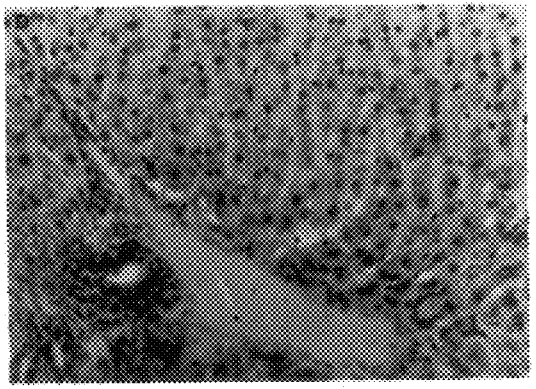
Figure 2E:
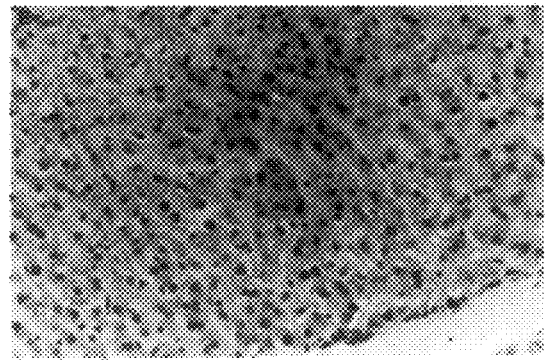
Figure 2F:
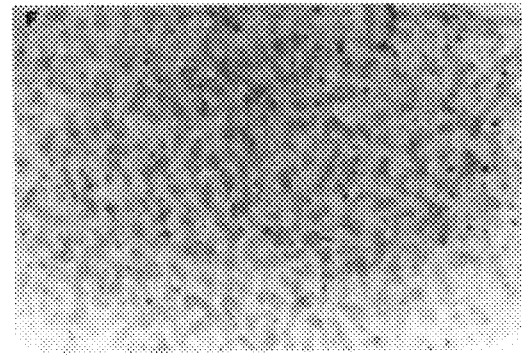

The presence of porcine hepatocytes in the WHHL rabbits was confirmed at autopsy by immunohistochemistry. Liver biopsies were fixed in 10% formalin and embedded in paraffin. Sections (5 µm) were prepared and stained with hematoxylin and eosin. Detection of secreted porcine albumin was accomplished using a specific anti-porcine albumin antibody. Antibody binding was visualized by a biotin-streptavidin peroxidase system (Biogenex) using AEC as the chromagen. Sections were taken randomly from various regions of the liver lobes. Negative controls were developed in the absence of primary antibody using adjacent tissue sections. Paraffin sections of transplanted WHHL rabbits were fixed and stained with a porcine specific anti-albumin IgG. The results of this experiment are illustrated in FIGS. 2A–2F. FIGS. 2A and 2B show the control tissues for pig and non-transplanted WHHL rabbit respectively. FIGS. 2C to 2F represent a time course following transplantation of porcine hepatocytes into the parenchyma of the recipient lobe. FIG. 2C is 1 hour post surgery. FIGS. 2D and 2E are 4 days after surgery. FIG. 2F is at 7 months after surgery. At the time of surgery the porcine cells are contained within the hepatic sinusoids (FIG. 2C). Two days after transplantation (FIG. 2D) the porcine hepatocytes can be seen adhering to and migrating into the endothelial lining of the vessels and adjacent parenchyma. After the graft has been established as indicated by long term lowering of serum cholesterol (FIG. 2E, R3530) numerous foci of cells are seen dispersed within the liver parenchyma where they appear to have integrated among the host cells.

Example III

Transplantation of Porcine Hepatocytes into Watanabe Heritable Hyperlipidemic Rabbits and Demonstration of Hepatocyte Function In Vivo Pre- and post-operative rabbit serum was collected from non-fasted animals using a morning bleed time for consistency. The serum was stored frozen. All sera were assayed for total serum cholesterol at a 1:1 or 1:2 dilution with physiologic saline by the cholesterol oxidase procedure. (Sigma Diagnostics, St. Louis, Mo.). Interassay variations for the cholesterol assay were 10–20%. Intra-assay variation was less then 10%. Reductions in serum cholesterol were noted within the first few weeks following transplantation. The results of this experiment are illustrated in FIG. 3. Rabbits were infused with $1-2\times10^8$ porcine hepatocytes via the portal vein. Total serum cholesterol levels were determined as described above. Pretransplant levels were: for rabbit R3738, 535±49 mg/dl; for rabbit R3779, 690±24 mg/dl; for rabbit R3777, 610±24 mg/dl; and for rabbit R4045, 800±26 mg/dl; R3728, 560±41 mg/dl. Rabbit R3739 was a sham surgery control with carrier only infused. Rabbit R3534 was a control rabbit that did not receive cyclosporin. All other rabbits were injected with cyclosporin (s.c.) at 10 mg/kg/day.

As shown in FIG. 3, reductions in total serum cholesterol reached 60–65% of pretransplant levels. All recipient animals achieved a 30–40% reduction within the first 10–15 days after transplantation. The mean serum cholesterol reduction for animals under immunosuppression remained at 40.4+/−5.6% of pretransplant levels for the 3–8 weeks after transplantation. An animal that was infused with porcine hepatocytes in the absence of cyclosporin administration (R3534) showed no sustained decrease in serum cholesterol. Cholesterol levels in a sham surgery animal (no cells infused) were reduced by a maximum of 10–20% over the same time interval. One rabbit transplanted with porcine hepatocytes showed no decrease in serum cholesterol.

Three WHHL rabbits were transplanted and monitored for longer time periods to determine the duration of serum cholesterol lowering. The results of this experiment are illustrated in FIG. 4. All animals received cyclosporin at 10 mg/kg/day. Total serum cholesterol values were determined as a function of time post-transplantation. Pretransplant values were as follows: for rabbit R3530, 635±27 mg/dl; for rabbit R3533, 730±20 mg/dl; and for rabbit R3736, 580±40 mg/dl; R3739, 615 mg/dl. As shown in FIG. 4, the decrease in serum cholesterol levels was sustained for 3 months following hepatocellular transplantation. Two of these animals (R3530, R3533) demonstrated maximum decreases in total serum cholesterol of 60%–70%.

Figure 5:
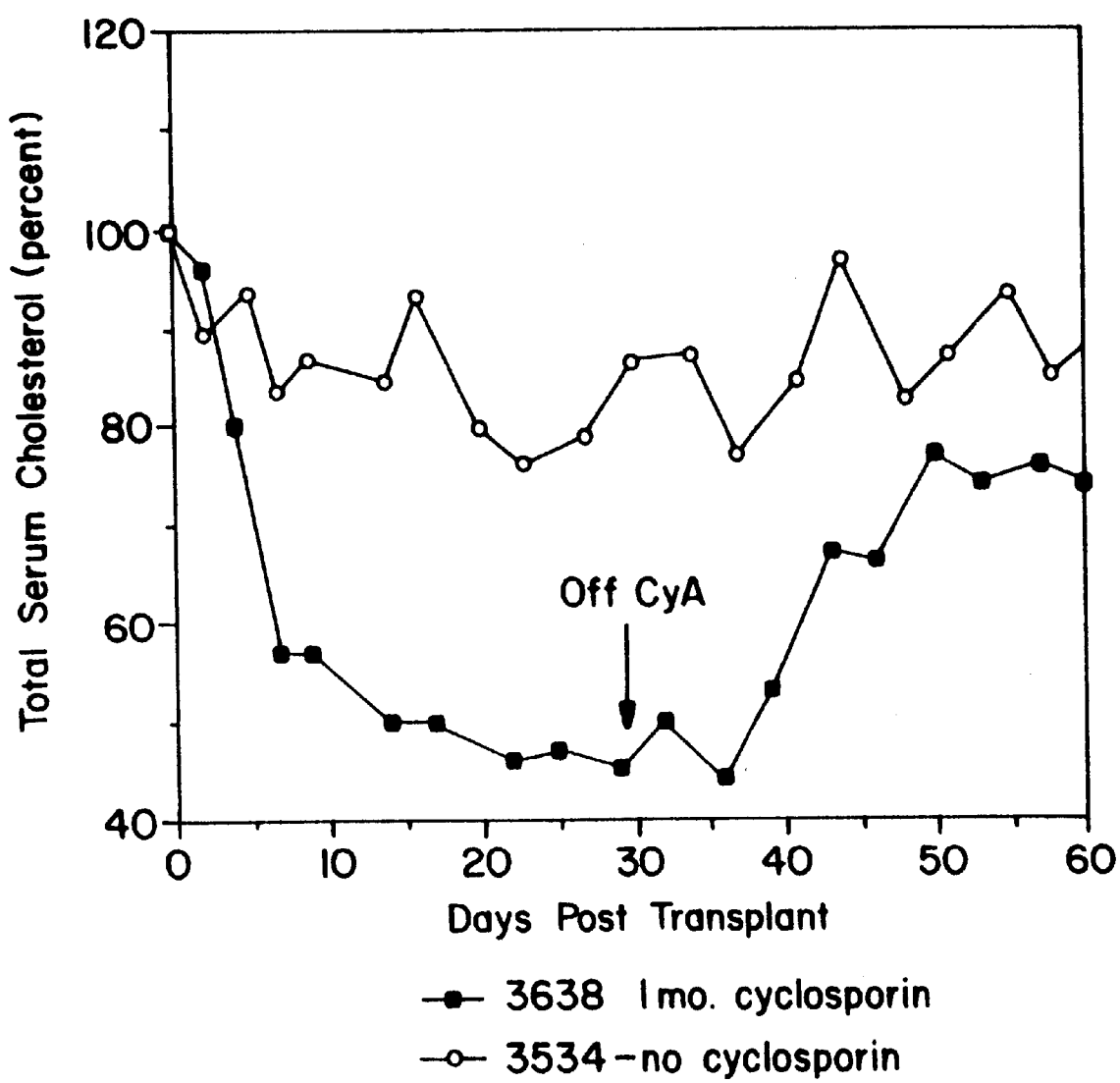
FIG. 5 is a graphic representation of the effect of cyclosporin therapy on hepatic graft survival as detected by decreases in total serum cholesterol in the WHHL rabbit.
Figure 6:
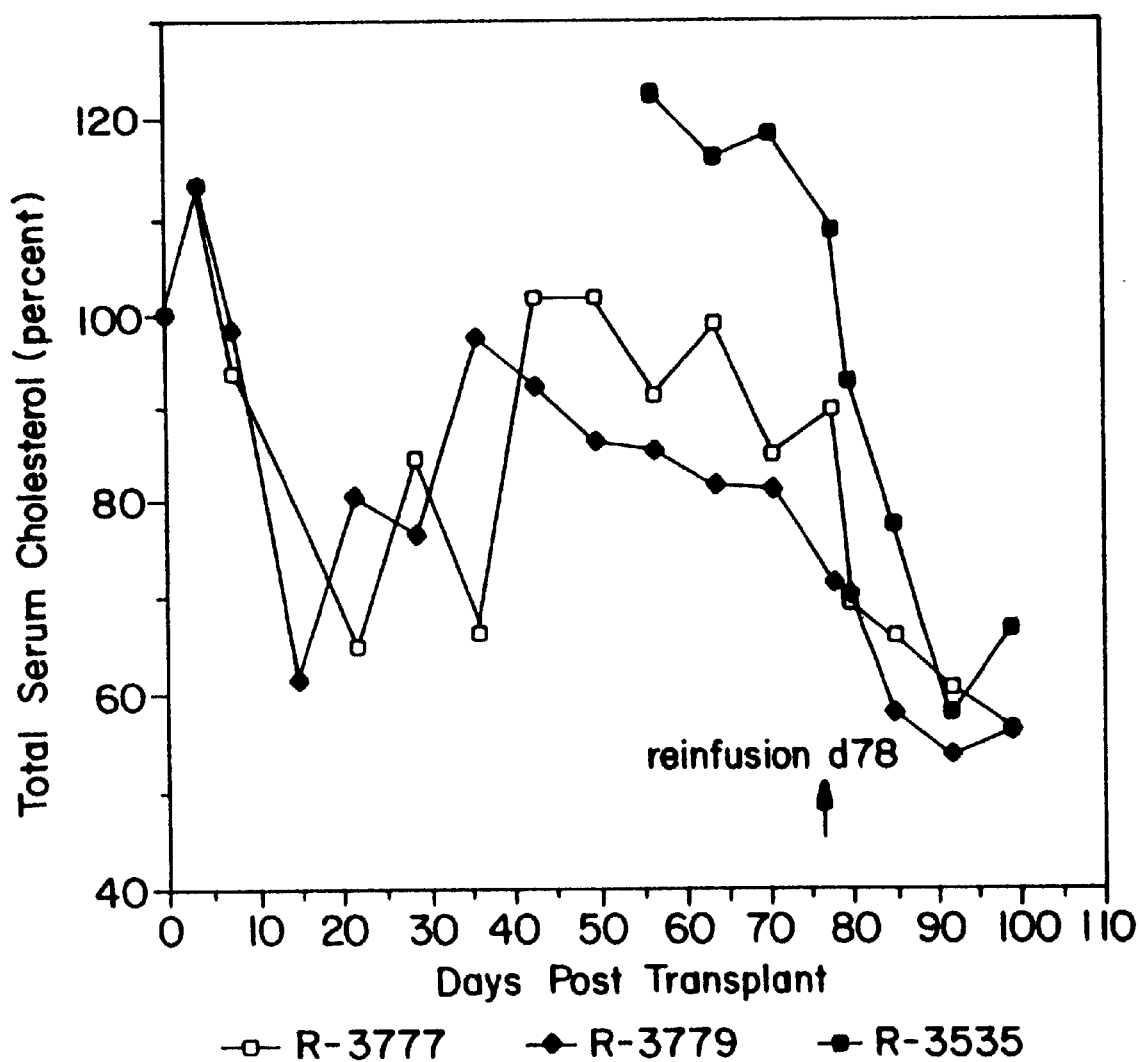
FIG. 6 is a graphic representation of total serum cholesterol levels in WHHL rabbits after a second porcine hepatocyte transplantation and cyclosporin treatment.

To confirm that the decrease in serum cholesterol was attributable to the transplanted porcine hepatocytes, a rabbit was removed from immunosuppression 30 days after transplantation. The results of this experiment are illustrated in FIG. 5. Animals had been treated with cyclosporin A at 10 mg/kg/day starting the day after transplantation. The arrow indicates the time after transplantation that the animal was taken off cyclosporin A treatment. As shown in FIG. 5, the cessation of cyclosporin administration resulted in a return of total serum cholesterol to pretransplant levels suggesting that rejection of the cells caused an increase in serum cholesterol. The increase in serum cholesterol values was apparent within the first 10 days of withdrawal of the drug. Also shown in FIG. 5 is a control rabbit that had not received cyclosporin in conjunction with the hepatocyte transplant. Rabbits receiving cyclosporin but no porcine hepatocytes showed no sustained reduction in serum cholesterol. Further decreases in serum cholesterol of WHHL rabbits could be achieved on reinfusion of porcine hepatocytes. The serum cholesterol levels in two WHHL rabbits (R3777, R3779) were decreased by approximately 40% over an initial 30 day time period after transplantation with porcine hepatocytes. In contrast to the rabbits shown in FIG. 3, these animals showed an increase in serum cholesterol starting at day 20–30. To determine whether further decreases in serum cholesterol could be achieved, a second infusion of $2\times10^8$ porcine hepatocytes was completed 78 days after the initial transplant. Both rabbits showed an immediate lowering of cholesterol levels (FIG. 6) that was sustained until at least 100 days after the initial transplant. A third animal, R3535, that had not been previously transplanted with porcine cells, was also infused and also showed an immediate lowering of cholesterol levels that was sustained 100 days after transplant. All animals received cyclosporin.

Figure 7:
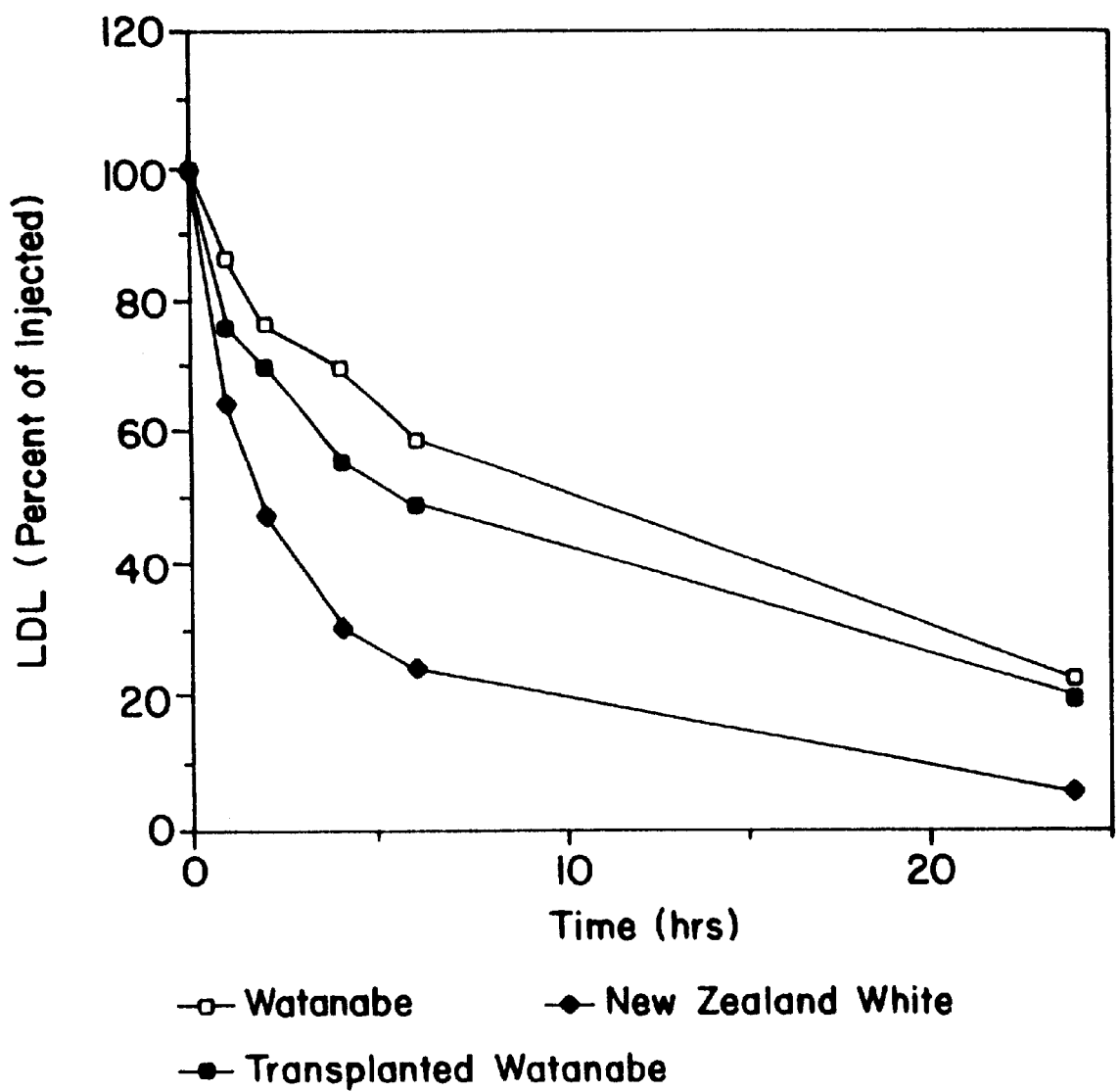
FIG. 7 is a graphic representation of the clearance of $^{125}$I-human low density lipoprotein (hLDL) from serum by a WHHL rabbit and a New Zealand White rabbit, neither of which was transplanted with porcine hepatocytes, and a WHHL rabbit transplanted with porcine hepatocytes and treated with cyclosporin.

To establish that the transplanted hepatocytes were functional and were responsible for the noted reductions in cholesterol levels, clearance studies were performed using iodinated human LDL. Labeled human LDL (20–40 µCi) was delivered via the marginal ear vein in physiological saline containing 2 mg/ml bovine serum albumin. Blood was collected from the opposite ear at intervals after injection. $^{125}$I-Apolipoprotein B-containing LDL was precipitated with isopropanol (Holmquist, L. et al. (1978) *Anal. Biochem.* 88:457–460; Lagrost, L. et al. (1989) *J. Lipid Res.* 30:701–710). Percent clearance from the plasma was determined from duplicate counts taking the 2 minute time point as 100%. The animals were not starved prior to this study. The experiments were designed to measure the differences in clearance rates of the diseased control (nontransplanted WHHL rabbit), normal control New Zealand White and transplanted WHHL rabbits. The results of this experiment are illustrated in FIG. 7. The WHHL rabbit transplanted with porcine hepatocytes showed a significant increase in the rate of LDL clearance relative to the nontransplanted WHHL rabbit. The time required for clearance of 50% of the serum $^{125}$I-hLDL was 10.5 hr for a control WHHL rabbit, 6 hours for a transplanted WHHL rabbit and 2.5 hours for a New Zealand White rabbit.

To determine the effect of hepatocellular transplantation on the relative levels of HDL, LDL/IDL and VLDL in the recipient animal, FPLC fractionation was undertaken. Serum samples (200 µl) from New Zealand White, pretransplant WHHL rabbit and post-transplant WHHL rabbit were fractionated by FPLC on a Superose HR6 column. (Pharmacia) in a buffer containing 0.15M NaCl, 0.01% EDTA, 0.02% $NaN_3$, 0.01M Tris-HCl, pH 7.4 (22,23). HDL and LDL peaks were identified using purified commercial lipoproteins (Organon Teknika, Rockville, Md.). The column was run at 0.4 ml/min. Fractions (0.6 ml) were collected and assayed for total serum cholesterol after lyophilization. The results of this experiment are illustrated in FIG. 8. The results in FIG. 8 show the lipoprotein profile of a WHHL rabbit at intervals after hepatocellular transplantation. A distinct lowering of the LDL/IDL-cholesterol level was observed with time, consistent with the decreases in total serum cholesterol. Decreases in cholesterol were also observed in the region of VLDL, presumably due to increased conversion to IDL/LDL and subsequent uptake. WHHL rabbits are characterized by low levels of serum HDL. This fraction was not detectable prior to transplantation but following porcine hepatocyte transplantation an HDL-cholesterol fraction became detectable (see inset FIG. 8)

Example IV

Transplantation of Masked Porcine Hepatocytes into Watanabe Heritable Hyperlipidemic Rabbits and Demonstration of Hepatocyte Function In Vivo To demonstrate that porcine hepatocytes which are modified by binding anti-MHC class I antibodies to the MHC class I antigens on their surface survive and function in a xenogeneic subject, porcine hepatocytes were incubated with F(ab')$_2$ fragments of PT-85, a mouse monoclonal antibody specific for porcine MHC class I. This incubation was performed in PBS for 1 hour at 4° C. with 1 µg antibody/10$^6$ cells. The hepatocytes having these antibodies bound to their MHC class I surface antigens are referred to hereinafter as "masked" hepatocytes. Control cells (unmasked) were incubated for the same time period in PBS or with a control F(ab')$_2$ fragment prepared from a monoclonal antibody (10–14) that binds to porcine CD-44. Prior to transplantation the cells were washed in Hanks solution at 4° C. to remove unbound antibody, and control cells were treated in the same way.

WHHL rabbits were transplanted with 2×10$^8$ masked porcine hepatocytes by portal vein infusion. Total serum cholesterol levels were determined as described in Example III. Pretransplant levels were: for rabbit R3531, 715 mg/dl; and for rabbit R3532, 670 mg/dl; R-4138, 970 mg/dl. Rabbit 4054 was a control animal that received porcine hepatocytes masked with 10–14, an irrelevant antibody. The results of this experiment are illustrated in FIG. 9. As shown in FIG. 9 reductions in total serum cholesterol were observed and these reductions were maintained for 80 days. Unmasked cells or cells incubated with control monoclonal antibody were rejected as manifested by a return of serum cholesterol to pre-transplant levels within two weeks after transplantation. Two animals that were transplanted with masked cells did not show reduced serum cholesterol levels; this may be associated with limitations of the surgical procedure. Several rabbits were treated with subtherapeutic cyclosporin for two weeks in conjunction with masking. Total serum cholesterol levels were determined as described in Example III. Pretransplant levels were: for rabbit R3741, 975 mg/dl; for rabbit R4046, 900 mg/dl; for rabbit R4139, 850 mg/dl; and for rabbit R4246, mg/dl. Two rabbits were injected with cyclosporin (s.c.) at 10 mg/kg/day for 14 days (ST) in combination with masking and two rabbits were injected with cyclosporin (s.c.) at 10 mg/kg/day for just one day (SD). The results of this experiment are illustrated in FIG. 10. As shown in FIG. 10, serum cholesterol levels of all four rabbits decreased. Again reductions in serum cholesterol were observed in the animals receiving masked cells. Five of eight animals treated with masked cells in combination with short term cyclosporin showed sustained serum cholesterol reductions of over 20%.

Clearance studies using iodinated human LDL were performed to determine whether the cholesterol reductions were attributable to increased LDL uptake. Intact LDL-cholesterol was precipitated from serum using isopropanol at intervals after the injection of the radiolabelled LDL. The results of this experiment are illustrated in FIG. 11. Rabbits were injected with $^{125}$I-hLDL at time 0. The time course of clearance was monitored following isopropanol precipitation of 0.5 ml of plasma with 100% defined as the $^{125}$Icpm precipitated at 3 minute post injection. The WHHL rabbit transplanted with masked porcine hepatocytes showed a significant increase in the rate of LDL clearance relative to the nontransplanted WHHL rabbit. The time required for clearance of 50% of the serum $^{125}$I-LDL was 21 hours for a control WHHL rabbit, 11 hours for a transplanted WHHL rabbit and 4 hours for a New Zealand White rabbit. This represents a two fold increase in the rate of LDL clearance in the WHHL rabbit transplanted with masked hepatocytes and indicates that the masked porcine cells remained functional and were responsible for the reduced serum cholesterol.

To determine the effect of hepatocellular transplantation on the relative levels of HDL, LDL/IDL and VLDL in the recipient animal, FPLC fractionation was undertaken. The results of this experiment are illustrated in FIG. 12. The lipoprotein profile of a WHHL rabbit at intervals after transplantation of masked hepatocytes is shown in FIG. 12. A distinct lowering of the LDL/IDL-cholesterol level was observed with time, consistent with the decreases in total serum cholesterol. Decreases in cholesterol were also observed in the region of VLDL, presumably due to increased conversion to IDL/LDL and subsequent uptake.

Figure 13A:
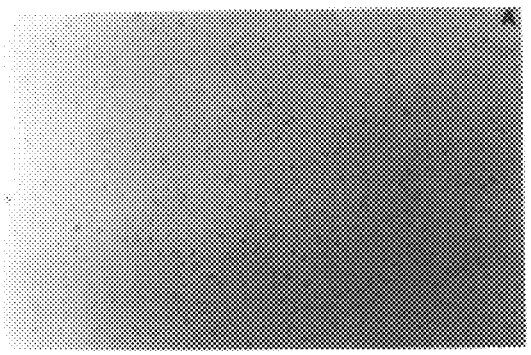
FIGS. 13A–13D show localization of porcine hepatocytes in liver sections from a WHHL rabbit transplanted with masked porcine hepatocytes by in situ hybridization using a porcine repeat element.
Figure 13B:
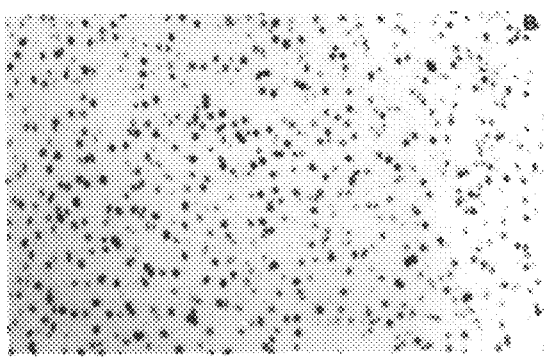
Figure 13C:
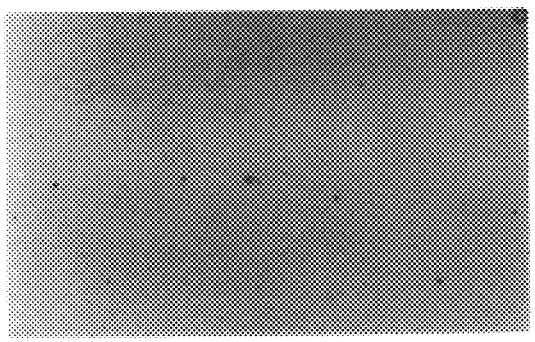
Figure 13D:
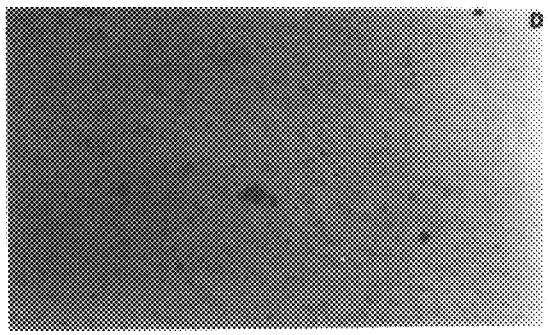

The transplanted masked porcine hepatocytes were detected in paraffin sections of WHHL rabbit liver by in situ hybridization using a probe that hybridizes with a pig specific repetitive element present in numerous copies in the pig genome. This 234 base pair fragment of DNA is specific for hybridization with pig DNA. Digoxygenin-labeled probe was hybridized to paraffin sections and staining was accomplished by incubation with alkaline phosphatase labeled antidigoxygenin antibody and 5-bromo-4-chloro-3'-indolylphosphate p-toluidine salt/nitro-blue tetrazolium chloride. The results of this experiment are illustrated in FIGS. 13A–13D. FIG. 13A shows control rabbit liver. FIG. 13B shows a pig liver hybridized with the probe. FIG. 13C (low magnification) and FIG. 13D (high magnification) are from a WHHL rabbit transplanted with masked porcine hepatocytes. After the graft had been established as indicated by long term lowering of serum cholesterol, numerous foci of cells were seen dispersed within the liver parenchyma where they appeared to have integrated among the host cells (FIGS. 13C and 13D).

Figure 14:
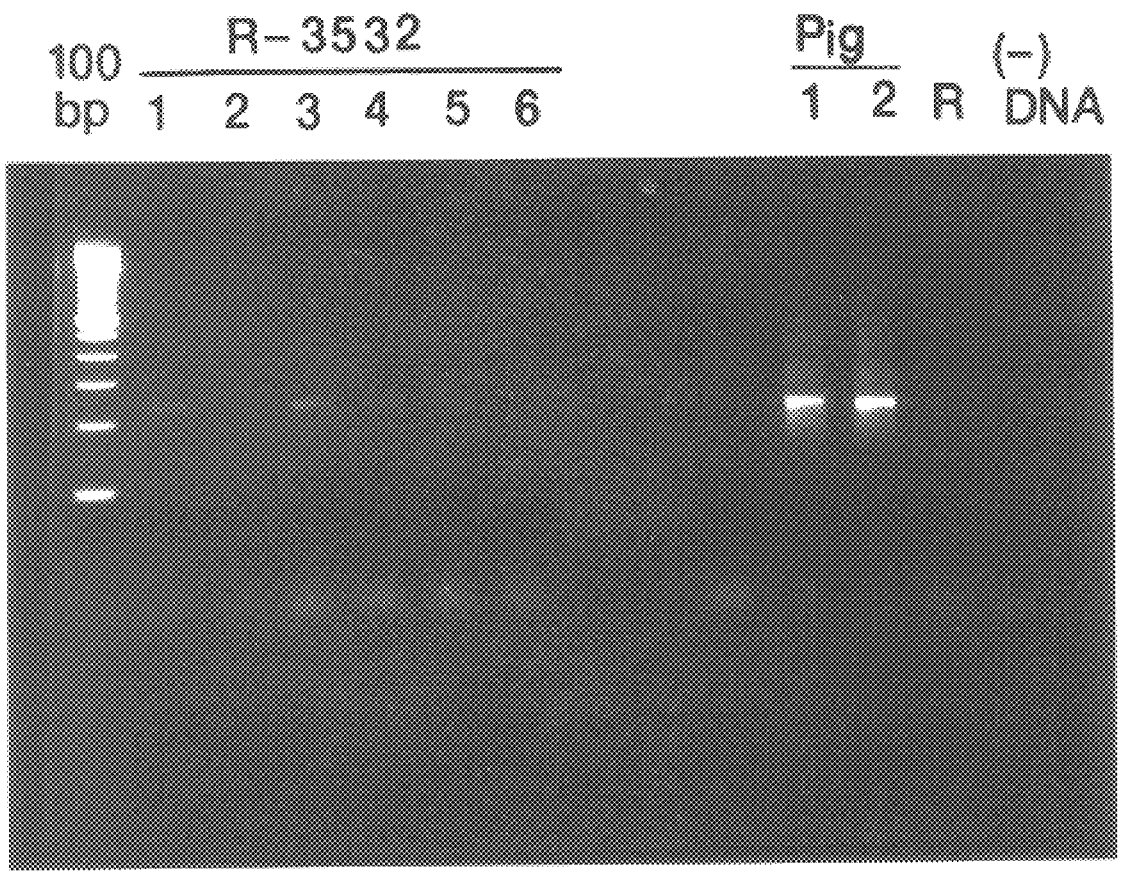
FIG. 14 is a blot illustrating the presence of porcine repeat element in DNA isolated from the liver of a WHHL rabbit transplanted with masked porcine hepatocytes nine months prior to sacrifice and a control WHHL rabbit.

As an additional way of determining whether porcine cells were present in the rabbit livers, a polymerase chain reaction (PCR)-based method of detection was developed using primers for the 234 base pair porcine repetitive element. Oettinger et al. (1995) *Cell Trans*. 4:235. Rabbit livers were frozen on dry ice and stored at –80° C. The tissue was thawed, cut into 2 mm$^3$ sections and digested with proteinase K for 18 hours at 65° C. After precipitation of protein the DNA was extracted. Samples containing 1 µg DNA were amplified by PCR using AmpliTaq (Perkin Elmer) for 30 cycles. The products were electrophoresed on a 2% agarose gel. The results shown in FIG. 14 demonstrate that pig cells were present in the transplanted livers. Pig specific bands are seen in 4 of 6 tissue sections from the WHHL rabbit (R-3532, six months post transplant). A non-transplanted rabbit liver (R) shows no band. Pig liver is the positive control.

Example V

Transplantation of Porcine Hepatocytes into Cirrhotic Rats and Demonstration of Hepatocyte Function In Vivo To evaluate the feasibility of hepatocyte transplantation for liver failure, the $CCl_4$ induced cirrhotic rat was used as a model system. Porcine hepatocytes ($2-4 \times 10^7$), isolated as described in Example I, were introduced into rats (n=12) by infusion into the spleen from which the cells rapidly entered the liver sinusoids via the splenic and portal veins. Portal hypertension did not present a surgical problem when these cell numbers were infused.

The transplanted porcine hepatocytes were observed in the liver sinusoids immediately following transplantation and in the liver parenchyma 7 days post transplantation when the animals were under cyclosporin immunosuppression. The porcine hepatocytes were visualized by both PRE in situ hybridization and porcine albumin immunohistochemistry. These data confirm that, as with the Watanabe rabbit liver, porcine hepatocytes are able to integrate into the cirrhotic rat liver.

Example VI

Transplantation of Porcine Hepatocytes into Cirrhotic Dogs and Demonstration of Hepatocyte Function In Vivo The Following Materials and Methods were used in Example VI:
Isolation and Viability of Porcine Hepatocytes GMP Yorkshire pigs are used as the liver donors. Each liver is excised and maintained in Belzer's transport media. Porcine hepatocytes are isolated by a modification of a two step perfusion method (Berry, M. N. and Friend, D. S. (1969) *J. Cell. Biol.* 43:506), involving an initial perfusion with Hanks Buffered Saline (no $Mg^{++}$ no $Ca^{++}$) containing 0.5 mM EDTA to disrupt the calcium dependent desmosomes. This is followed by a collagenase perfusion in the presence of $Ca^{++}$ at 37° C. Following digestion, the cells are released from the cytoskeleton by physical disruption. Cells are washed at 4° C. in DMEM/Weymouth (3:1) medium containing 10% calf serum to stop the digestion. Isolated hepatocytes are resuspended in completed Hanks Buffered Saline and prepared for transplantation. Porcine hepatocytes are routinely above 85% viable by trypan blue staining.

A portion of the isolated cells are plated in DMEM/Weymouth (3:1) containing 10% fetal calf serum for further viability and functionality testing. Cells are scored for their plating efficiency, lactate dehydrogenase (LDH) release and production of porcine albumin/time/ng DNA. Cells analyzed for non-hepatocyte (Kuppfer, endothelial) content by immunohistochemistry using an anti-porcine MHC class II antibody have indicated less then 2% contamination.

Fetal porcine hepatocytes are also used. Fetal hepatocytes are isolated from 38 day fetus by dissection of the fetal liver followed by mincing and collagenase (1.5 mg/ml) digestion at 37° C. for 30 min. The resultant hepatocytes are washed in 10% fetal calf containing medium (DMEM, 4° C.) at 50 rpm for 5 min. The cells are plated at $2 \times 10^5$ cells/cm$^2$ in the same medium. Cells are allowed to attach overnight and the following day the cells are washed to remove red blood cells and non-viable cells. Fetal hepatocytes can be expanded in culture or used for transplantation. A fetal (38d) hepatocyte isolation yields approximately $10^8$ cells. One advantage of using fetal hepatocytes in the cirrhotic rat and dog models is the reduced number of cells that have to be transplanted due to their proliferative capacity in the regenerative environment.

Cirrhotic Dog Model

Fourteen adult male beagles are used as the large animal model for the evaluation of safety and efficacy of porcine xenografts. Dogs are housed in the Laboratory Animal Science Center with a 24 hour light/dark cycle and free access to food and water.

Cirrhosis is induced by two mechanisms with 6 dogs and 8 dogs per group, respectively:

1) Biliary cirrhosis: standard bile duct ligation after cholecystectomy is performed using a laparoscopic approach to minimize animal discomfort and pain (Reichen, J. and Simon, F. R. in The Liver: Biology and Pathobiology (Raven Press, N.Y., 1994) 1291–1326). This model results in cirrhosis with ascites in approximately 12 weeks and is used for studies of the method of delivery of hepatocytes and improvement in clinical parameters. Since the bile duct ligation is essentially irreversible and hepatocyte damage continues, this model is representative of cirrhosis with continuing hepatocyte injury; and 2) Chemical cirrhosis: an hepatotoxin, dimethylnitrosamine (DMNA) is added twice weekly (gelatin capsule of 0.2 ml /Kg) to dog chow to produce experimental central-portal fibrosis. There is little or no resolution of fibrosis after stopping DMNA and this model represents a stable end-stage cirrhosis without ongoing hepatocyte injury. Cirrhosis develops after 13 weeks and is monitored by liver biopsy. This model is a good model for long term study of xenografts, clinical parameters of liver failure, and survival. The monitoring of the progression of the cirrhosis is performed as follows: during the induction phase, monthly serum liver function tests, prothrombin time assays and serum ammonia levels are measured. Cirrhosis is diagnosed when ascites occurs clinically and is confirmed by liver biopsy.

Treatment of Hepatocytes with MHC Class I $F(ab')_2$ Fragments $F(ab')_2$ fragments are prepared from a monoclonal antibody PT-85 which is specific for porcine MHC class I (Ivanoska, D. et al. (1991) *Immunogenetics* 33:220–223; Davis, W. C. et al. (1987) *Vet. Immunol. and Immunogen* 15:337–376) by pepsin digestion (Pierce, immobilized pepsin) and purified by protein A-Sepharose chromatography (Davis, W. C. et al. (1987) *Vet. Immunol. and Immunogen* 15:337–376; Parham, P. in Handbook for Immunology (Blackwell, London, 1984) 14.1–14.23). The purity of the preparation is assessed by SDS polyacrylamide gel electrophoresis with silver staining. FACS scanning is then utilized to determine the amount of $F(ab')_2$ fragments required to saturate all sites on hepatocytes by titration against a fixed number of cells in time periods of 0.5 to 2 hours. Titration of hepatocytes with the anti-MHC antibodies yields 50% saturation at 0.1 µg of antibody per $10^6$ cells. The expression of MHC class I on these cells is lower than found on porcine lymphocytes and endothelial cells, consistent with reports of MHC class I expression on hepatocytes (Bumgardner, G. L. et al. (1990) *Transplantation* 49:429–436).

Freshly isolated hepatocytes are incubated with a 10 fold excess (1 µg/10$^6$ cells) of the F(ab')$_2$ fragments of PT-85 in PBS. This treatment is carried out for 1 hour at 4° C. Prior to transplantation, the cells are washed in Hanks solution at 4° C. to remove unbound antibody. The animals receive cyclosporin at 10 mg/kg/day and serum cyclosporin levels are monitored.

Biliary Cirrhosis Model

These studies elucidate the effect of hepatocyte transplantation on clinical liver disease, portal hemodynamics, and survival in a model of continuing chronic hepatocellular injury.

The following two techniques are used to introduce hepatocytes into the host liver:

1) percutaneous transhepatic portography with gelfoam embolization of collateral's followed by infusion of hepatocytes. This technique minimizes risk of hepatocyte shunting away from the liver but does not lower portal pressure post transplant; and 2) transjugular cannulation of portal vein, hepatocyte infusion followed by placement of a transjugular intra-hepatic porto-systemic shunt (TIPS) (Rossle, M. and Ring, E. J. in Progress in Liver Disease (Saunders, 1994) Vol. XII;177–189) with resulting fall in portal pressure. There are two animals in each group, one animal receives adult and the other animal receives fetal porcine hepatocytes. A 3rd group receives TIPS only without hepatocytes to act as control group.

Clinical Monitoring

Standard clinical assays are performed to evaluate graft function, portal hemodynamics and survival post-transplantation. Pre- and post transplantation AST, ALT, bilirubin, albumin, PT, serum ammonia, urinary sodium, creatinine and electrolytes are performed twice a week.

Liver Biopsy

Liver biopsies are performed at days 3, 7, and 28 to evaluate histological integration of porcine hepatocytes by immunohistochemistry using antibodies to porcine specific albumin and MHC class I antigen. Other methods for detection of hepatocytes include a newly developed PCR method for porcine repetitive element which is quantitative and in situ hybridization procedure. These methods are described below.

Portal Pressure Studies

Measurement of portal pressure is performed immediately before and after hepatocyte infusion when the cannula is in the portal vein using a Hewlett-Packard pressure transducer and recorder. Repeat studies at the time of liver biopsy are performed at days 3, 7, and 28 via transhepatic portography to observe long and short term effect of transplantation on portal hemodynamics and to evaluate TIPS function.

Encephalopathy Stress Test

Spontaneous encephalopathy is unusual in dogs but can be induced by porta-caval shunting in cirrhotic animals and by protein loading. Dog encephalopathy can be clinically evaluated by abnormal behavior such as hypersalivation, abnormal gait, rigidity, intent gaze and occasionally stupor and coma. At days 2, 10 and 21 dogs are fed increasing concentrations of protein until clinical encephalopathy is apparent.

Detection of Transplanted Porcine Hepatocytes

The survival of the transplanted cells in the dogs is assessed by three approaches:

1) determination of their secretory function in the transplanted animals;

2) direct visualization of the cells in the graft by immunohistochemistry and by in situ hybridization; and 3) analysis for porcine cells in graft biopsies by polymerase chain reaction to amplify a pig specific repetitive DNA element.

These assessments are accomplished by serial bleeding of the animals at various times after transplantation (daily for the first 3 days and weekly thereafter), by biopsies of the dog liver at intervals after transplantation, and by sectioning of the liver after sacrifice of the animals. Upon termination of the experiments, the livers are examined for gross and histopathology as well as immunohistochemistry and in situ hybridization to identify the porcine cells.

Porcine Albumin Secretion

The ability to detect porcine albumin in the transplanted model is dependent upon the number of cells that are injected, the number of recipient cells capable of cell division, and the extent to which both cells types respond to the hepatotropic factors in the serum. Hepatotropic factors such as HGF do not have a strict species dependency (Zioncheck, T. F. et al. (1994) *Endocrinology* 134(4): 1879–1887) and thus it is expected that the porcine cells will respond to the dog growth factors. The sensitivity of the ELISA assay is 100 ng/ml and the transplantation of 1% of the liver mass should result in the production of sufficient porcine albumin to be detectable.

Species-specific antibodies for porcine albumin have been prepared by immunoabsorption of anti-porcine albumin sera on a matrix of mouse albumin coupled to cyanogen bromide activated Sepharose 4B. The sera obtained do not cross react with the dog proteins and is used to measure the secretion of porcine albumin from the graft. For ELISA, the species-specific antibody is used to detect the transplanted cell products on microtiter plates, with biotinylated goat anti-rabbit IgG and streptavidin HRP for detection. The ELISA for albumin has been developed in the laboratory and has been shown to be highly specific for porcine albumin. The lack of cross-reactivity of these antibodies with recipient proteins has been checked by Western blotting.

Immunohistological Analysis to Detect Porcine Hepatocytes

At the end of the experiment, the dogs are sacrificed and their livers preserved in formalin. Paraffin sections of the dog liver are prepared for histology and examined for pathology. The porcine cells in the sections are detected by immunohistochemistry using porcine specific antibodies developed for the identification of porcine hepatocytes in the liver of the rabbit. The section is first incubated with a pig-specific anti-albumin antibody. The primary antibody is reacted with biotinylated goat anti-rabbit IgG (DAKO), and detection is achieved with streptavidin peroxidase and amino-ethylcarbazole. A second antibody used to detect the porcine cells is a monoclonal antibody against porcine MHC class I (Diacrin, Charlestown, Mass.). Antibody 9-3 is employed as the primary antibody with biotinylated goat anti-mouse IgG as the secondary antibody.

In Situ Hybridization Detection of Porcine Cells

Tissue fixed in Bouin's fixative is sectioned (4µ) and heat dried for one hour. Sections are deparaffinized and treated for 30 min with 2.5 mg/ml proteinase K at 37° C. After rinsing in sodium citrate/saline, slides are dehydrated through an ethanol series and air dried. For hybridization, a plasmid probe is used which contains a 234 base pair repeat element that has been cloned by PCR (Oettinger, H. F. et al. (1995) *Cell. Transplant.* 4:253–256). The product was cloned into a T-tailed vector and labeled with digoxygenin using a commercial kit (Boehringer Mannheim). The plasmid is added to the slides in 50% formamide. Following denaturation at 100° C. for 10 min, hybridization is performed overnight at 37° C. After equilibration in Tris-HCl, the slides are incubated with an alkaline phosphatase conjugated monoclonal antibody against digoxygenin. Development is accomplished with BCIP/NBT.

Analysis of Dog Liver Biopsies for Porcine Cells by Semi-Quantitative PCR Using Porcine Repetitive Element DNA The dog liver biopsies are frozen on dry ice and stored at −80° C. The tissue is thawed, cut into 2 mm$^3$ sections and digested with proteinase K for 18 h at 65° C. The cell lysate is digested with RNase and protein is precipitated prior to precipitation of the DNA with isopropanol. The total DNA concentration is determined ($A_{260}$) and 1 μg is taken for PCR. To determine whether pig DNA is present in the dog tissue, the extracted DNA is employed as target for 30 cycles of PCR with AmpliTaq DNA polymerase, dNTPs and primers for the 234 base pair porcine repetitive element (Oettinger, H. F. et al. (1995) *Cell. Transplant.* 4:253–256). The following primers are used: 5':AGGGAGTTC-CCATCGTGGCTCAG; and 3':AGGGCCNCACCCGCG-GCATATGGA. The products are electrophoresed on 2% agarose gels.

The results from these studies show xenograft and total liver function and portal hemodynamics with and without TIPS in active cirrhosis. Comparison of Groups 1 and 2 shows the effect of portal pressure on graft integration and function. Comparison of Groups 2 and 3 demonstrates whether hepatocyte transplant is able to improve TIPS associated encephalopathy. Comparison of Groups 1 and 2 versus Group 3 demonstrates clinical efficacy of the hepatocyte transplant.

Chemical Cirrhosis Model

This model is used to mimic cirrhosis without severe ongoing fibrosis or hepatocellular injury. Using this model, the potential number of transplants, role and timing of TIPS in transplantation and the efficacy of transplantation for prolonged liver function and survival are evaluated. Animals are again divided into 4 groups: Group 1 receives TIPS first, followed 1 week later by transhepatic cannulation of portal vein and infusion of hepatocytes; Group 2 receives TIPS and hepatocyte infusion concomitantly; Group 3 receives transhepatic cannulation of portal vein, embolization of collateral's and hepatocyte transplant without TIPS. One animal in each group receives adult and one animal in each groups receives fetal porcine hepatocytes. Group 4 is treated with TIPS only without hepatocytes to serve as a control. Clinical monitoring is performed as described herein.

Repeat Transplantation

The porcine albumin ELISA is used to monitor xenograft function and when this shows a steady decline over 2 measurements two days apart, repeated transplantation through a transhepatic approach is used for up to a maximum of three times per animal. After each transplant, clinical monitoring is performed as described above.

Evaluation of Mitotic Activity in the Recipient Liver

Since the therapeutic effect of hepatocyte transplantation results from the restoration of liver function through restoration of sufficient liver cell mass, the ability of the transplanted cells to divide as well as the recipient cells to regenerate is of prime concern. Cell division plays a prominent role in the transplantation of fetal porcine hepatocytes.

To estimate the mitotic activity of the transplanted liver cells, the thymidine analog BrdU is used. Enhanced mitotic activity has been reported in cases of liver regeneration following partial hepatectomy and toxic insult. Paraffin sections are scored for the incorporation of BrdU using a monoclonal anti-BrdU antibody by an indirect immunoperoxidase method (Magaud, J. P. et al. (1988) *J. Immunol. Methods* 106:95–100). The degree of mitotic activity (grain counting) is compared with the number of transplanted cells detected by semi-quantitative PCR. The presence of cell numbers higher than expected from preliminary early time point PCR analysis is indicative of cell division of transplanted porcine hepatocytes. Alternatively, a commercially available monoclonal antibody to HGF is used to determine the presence of hepatotropic factors in the liver. The identification of active liver regeneration and/or division is reflected in enhanced graft expansion and reversal of liver failure.

Example VII

Methods of Producing Essentially Pathogen-Free Swine from which Hepatocytes of the Invention can be Obtained A. Collecting, Processing, and Analyzing Pig Fecal Samples for Signs of Pathogens Feces are extracted from the pig's rectum manually and placed in a sterile container. About a 1.5 cm diameter portion of the specimen was mixed thoroughly in 10 ml of 0.85% saline. The mixture is then strained slowly through a wire mesh strainer into a 15 ml conical centrifuge tube and centrifuged at 650×g for 2 minutes to sediment the remaining fecal material. The supernatant is decanted carefully so as not to dislodge the sediment and 10% buffered formalin was added to the 9 ml mark, followed by thorough mixing. The mixture is allowed to stand for 5 minutes. 4 ml of ethyl acetate is added to the mixture and the mixture is capped and mixed vigorously in an inverted position for 30 seconds. The cap is then removed to allow for ventilation and then replaced. The mixture is centrifuged at 500×g for 1 minute (four layers should result: ethyl acetate, debris plug, formalin and sediment). The debris plug is rimmed using an applicator stick. The top three layers are carefully discarded by pouring them off into a solvent container. The debris attached to the sides of the tube is removed using a cotton applicator swab. The sediment is mixed in either a drop of formalin or the small amount of formalin which remains in the tube after decanting. Two separate drops are placed on a slide to which a drop of Lugol's iodine is added. Both drops are coverslipped and carefully examined for signs of pathogens, e.g., protozoan cysts of trophozoites, helminth eggs and larvae. Protozoan cyst identification is confirmed, when required, by trichrome staining.

B. Co-cultivation Assay for Detecting the Presence of Human and Animal Viruses in Pig Cells Materials:

Cell Lines

African green monkey kidney, (VERO), cell line American Type Culture Collection, (ATCC CCL81), human embryonic lung fibroblasts, (MRC-5) cell line American Type Culture Collection, (ATCC CCL 171), porcine kidney, (PK-15), cell line American Type Culture Collection, (ATCC CRL 33), porcine fetal testis, (ST), cell line American Type Culture Collection, (ATCC CRL 1746).

Medium, Antibiotics, and Other Cells, and Equipment

Fetal calf serum, DMEM, Penicillin 10,000 units/ml, Streptomycin 10 mg/ml, Gentamicin 50 mg/ml, guinea pig erythrocytes, chicken erythrocytes, porcine erythrocytes, Negative Control (sterile cell culture medium), Positive Controls: VERO and MRC-5 Cells: Poliovirus type 1 attenuated, (ATCC VR-192) and Measles virus, Edmonston strain, (ATCC VR-24), PK-15 and ST Cells: Swine influenza type A, (ATCC VR-99), Porcine Parvovirus, (ATCC VR-742), and Transmissible gastroenteritis of swine, (ATCC VR-743). Equipment: tissue Culture Incubator, Inverted Microscope, Biological Safety Cabinet.

These materials can be used in a co-cultivation assay (a process whereby a test article is inoculated into cell lines (VERO, MRC-5, PK-15, and ST) capable of detecting a broad range of human, porcine and other animal viruses). Hsuing, G. D., "Points to Consider in the Characterization of Cell Lines Used to Produce Biologicals" in Diagnostic Virology, 1982 (Yale University Press, New Haven, Conn., 1982).

Experimental Design and Methodology

A total of three flasks (T25) of each cell line are inoculated with at least 1 ml of test article. Three flasks of each cell line can also be inoculated with the appropriate sterile cell culture medium as a negative control. Positive control viruses are inoculated into three flasks of each cell line. After an absorption period, the inoculate is removed and all flasks incubated at 35–37° C. for 21 days. All flasks are observed at least three times per week for the development of cytopathic effects, (CPE), of viral origin. Harvests are made from any flasks inoculated with the test article that show viral CPE.

At Day 7 an aliquot of supernatant and cells from the flasks of each test article are collected and at least 1 ml is inoculated into each of three new flasks of each cell line. These subcultures are incubated at 35–37° C. for at least 14 days. All flasks are observed and tested as described above.

At Day 7, the flasks from each test article are also tested for viral hemadsorption, (HAd), using guinea pig, monkey and chicken erythrocytes at 2–8° C. and 35–37° C. at 14 days postinoculation.

At Day 21, if no CPE is noted, an aliquot of supernatant from each flask is collected, pooled, and tested for viral hemagglutination, (HA), using guinea pig, monkey, and chicken erythrocytes at 2–8° C. and 35–37° C. Viral identification is based on characteristic viral cytopathic effects (CPE) and reactivity in HA testing.

The test samples are observed for viral cytopathic effects in the following manner: All cultures are observed for viral CPE at least three times each week for a minimum of 21 days incubation. Cultures are removed from the incubator and observed using an inverted microscope using at least 40× magnification. 100× or 200× magnification is used as appropriate. If any abnormalities in the cell monolayers, including viral CPE, are noted or any test articles cause total destruction of the cell monolayer, supernatant and cells are collected from the flasks and samples are subcultured in additional flasks of the same cell line. Samples can be stored at −60° to −80° C. until subcultured. After 7 and 14 days incubation, two blind passages are made of each test article by collecting supernatant and cells from all flasks inoculated with each sample. Samples can be stored at −60° to −80° C. until subcultured.

Hemadsorbing viruses are detected by the following procedure: after 21 days of incubation, a hemadsorption test is performed on the cells to detect the presence of hemadsorbing viruses. The cells are washed 1–2 times with approximately 5 mls of PBS. One to two mls of the appropriate erythrocyte suspension (either guinea pig, porcine, or chicken erythrocytes), prepared as described below, is then added to each flask. The flasks are then incubated at 2–8° C. for 15–20 minutes, after which time the unabsorbed erythrocytes are removed by shaking the flasks. The erythrocytes are observed by placing the flasks on the lowered stage of a lab microscope and viewing them under low power magnification. A negative result is indicated by a lack of erythrocytes adhering to the cell monolayer. A positive result is indicated by the adsorption of the erythrocytes to the cell monolayer.

Hemagglutination testing, described in detail below, is also performed after 21 days of incubation of the subcultures. Viral isolates are identified based on the cell line where growth was noted, the characteristics of the viral CPE, the hemadsorption reaction, and hemagglutination reactions, as appropriate. The test article is considered negative for the presence of a viral agent, if any of the cell lines used in the study demonstrate viral, CPE, HA, or HAd in a valid assay.

C. Procedure for Preparing and Maintaining Cell Lines Used to Detect Viruses in Pig Cells Materials:

Fetal calf serum (FCS), DMEM, Penicillin 10,000 unit/ml, Streptomycin 10 mg/ml, Gentamicin 50 mg/ml, T25 tissue culture flasks, tissue culture incubator (5% $CO_2$, 37° C.)

Procedure:

Aseptic techniques are followed when performing inoculations and transfers. All inoculations and transfers are performed in a biological safety cabinet. Media is prepared by adding 10% FCS for initial seeding, 5% FCS for maintenance of cultures, as well as 5.0 ml of penicillin/streptomycin and 0.5 ml of gentamicin per 500 ml media. Sufficient media is added to cover the bottom of a T25 tissue culture flask. The flask is seeded with the desired cell line and incubated at 37° C., 5% $CO_2$ until cells are 80 to 100% confluent. The flasks are then inoculated with virus (QCP25).

D. Preparation of Erythrocyte (rbc) Suspensions Used in Hemadsorption (HAd) and Hemagglutination (HA) Virus Detection Testing Materials:

Phosphate buffered saline, (PBS), pH 7.2, guinea pig erythrocytes stock solution, porcine erythrocytes stock solution, chicken erythrocytes stock solution, sterile, disposable centrifuge tubes, 15 or 50 ml Laboratory centrifuge Procedure:

An appropriate amount of erythrocytes (rbc) is obtained from stock solution. The erythrocytes are washed 3 times with PBS by centrifugation at approximately 1000×g for 10 minutes. A 10% suspension is prepared by adding 9 parts of PBS to each one part of packed erythrocytes. The 10% rcb suspensions are stored at 2–8° C. for no more than one week. 0.5% ecb suspensions are prepared by adding 19 parts of PBS to each one part of 10% rbc suspension. Fresh 0 5% rbc suspensions are prepared prior to each day's testing.

Hemagglutination (HA) Test

A hemagglutination test is a test that detects viruses with the property to agglutinate erythrocytes, such as swine influenza type A, parainfluenza, and encephalomyocarditus viruses, in the test article. Hsuing, G. D. (1982) Diagnostic Virology (Yale University Press, New Haven, Conn.);. Stites, Daniel P and Terr, Abba I, (1991), Basic and Clinical Immunology (Appleton & Lange, East Norwalk, Conn.).

Materials:

Supernatants from flasks of the VERO cell line, MRC-5 inoculated with the test article, flasks of positive and negative controls, phosphate buffered saline (PBS), pH 7.2, guinea pig erythrocytes (GPRBC), 0.5% suspension in PBS, chicken erythrocytes (CRBC), 0.5% suspension in PBS, porcine erythrocytes (MRBC), 0.5% suspension in PBS Procedure:

All sample collection and testing is performed in an approved biological safety cabinet. 0.5% suspensions of each type of erythrocytes are prepared as described above. The HA test on all cell lines inoculated with samples of the test articles at least 14 days post-inoculation. Positive and negative control cultures are included for each sample and monolayers are examined to ensure that they are intact prior to collecting samples.

At least 1 ml of culture fluid from each flask inoculated with the test article is collected and pooled. 1 ml samples from the negative and positive control cultures are also collected and pooled. A set of tubes is labeled with the sample number and type of erythrocyte (distinguish positive and negative suspension) to be added. Racks may be labeled to differentiate the type of erythrocyte. 0.1 ml of sample is added to each tube. 0.1 ml of the appropriate erythrocyte suspension is added to each tube. Each tube is covered with parafilm and mixed thoroughly. One set of tubes is incubated at 2–8° C. until tight buttons form in the negative control in about 30–60 minutes. Another set of tubes is incubated at 35–37° C. until tight buttons form in the negative control in about 30–60 minutes.

Formation of a tight button of erythrocytes indicates a negative result. A coating of the bottom of the tube with the erythrocytes indicates a positive result.

E. Methods Used for Fluorescent Antibody Stain of Cell Suspensions Obtained from Flasks Used in Detection of Viruses in Porcine Cells Using Cell Culture Techniques (as Described in Sections B and C)

Materials:

Pseudorabies, parvovirus, enterovirus, adenovirus, transmissible Gastroenteritis Virus. bovine viral diarrhea, encephalomyocarditus virus, parainfluenza, vesicular stomatitis virus., microscope slides, PBS, incubator with humidifying chamber at 36° C., Evan's blue coutner stain, DI Water, fluorescent microscope, trypsin, serum containing media, acetone, T25 Flask.

Procedure:

Cells (described in Sections B and C) are trypsinized to detach them from the T25 flask and sufficient media is added to neutralize trypsin activity. A drop of cell suspension is placed on each microscope slide and allowed to air dry. A slide for each fluorescent antibody is prepared. Cells are fixed by immersion in acetone for five minutes. Each fluorescent antibody solution is placed on each slide to cover cells and the slides are incubated in humidifying chamber in incubator at 36° C. for 30 minutes. The slides are then washed in PBS for five minutes. The wash is repeated in fresh PBS for five minutes followed by a rinse with DI water.

The cells are counterstained by placing Evan's blue solution on each slide to cover cells for five minutes at room temperature. The slides are then washed in PBS for five minutes. The wash is repeated in fresh PBS for five minutes followed by a rinse with DI water. The slides are then allowed to air dry. Each slide is inspected under a fluorescent microscope. Any fluorescent inclusion bodies characteristic of infection are considered a positive result for the presence of virus.

F. Procedures for Defining Bacteremic Pigs

Materials:

Anaerobic BMB agar (5% sheep blood, vitamin K and hemin [BMB/blood]), chocolate Agar with Iso Vitalex, Sabaroud dextrose agar/Emmons, 70% isopropyl alcohol swabs, betadine solution, 5% $CO_2$ incubator at 35–37° C., anaerobic blood agar plate, gram stain reagents (Columbia Broth Media), aerobic blood culture media (anaerobic brain heart infusion with vitamin K& hemin), septicheck media system, vitek bacterial identification system, laminar flow hood, microscope, and bacteroids and Bacillus stocks Procedure:

Under a laminar flow hood, disinfect the tops of bottles for aerobic and anaerobic blood cultures of blood obtained from pig with 70% isopropyl alcohol, then with betadine The rubber stopper and cap from the aerobic blood culture bottle are removed and a renal septicheck media system is attached to the bottle. The bottles are incubated in 5% $CO_2$ for 21 days at 35–37° C., and observed daily for any signs of bacterial growth (i.e. gas bubbles, turbidity, discoloration or discrete clumps). Negative controls consisting of 5cc of sterile saline in each bottle and positive controls consisting of Bacillus subtilis in the aerobic bottle and Bacteriodes Vulgaris in the anaerobic bottle are used. If signs of bacterial growth are observed, a Gram stain is prepared and viewed microscopically at 100× oil immersion for the presence of any bacteria or fungi. The positive bottles are then subcultured onto both chocolate agar plates with Iso Vitlex and onto BMB plates. The chocolate plate is incubated at 35–37° C. in 5% $CO_2$ for 24 hours and the BMB anaerobically at 35–37° C. for 48 h yeast or fungi that is in evidence at gram stain is subcultured onto a Sabaroud dextrose/Emmons plate. The Vitek automated system is used to identify bacteria and yeast. Fungi are identified via their macroscopic and microscopic characteristic. If no signs of growth are observed at the end of 21 days, gram stain is prepared and observed microscopically for the presence of bacteria and fungi.

Absence of growth in the negative control bottles and presence of growth in the positive control bottles indicates a valid test. The absence of any signs of growth in both the aerobic and anaerobic blood culture bottles, as well as no organisms seen on gram stain indicates a negative blood culture. The presence and identification of microorganism(s) in either the aerobic or anaerobic blood culture bottle indicates of a positive blood culture; this typically is due to a bacteremic state.

Equivalents

Those skilled in the art will recognize, or be able to ascertain using no more than routine experimentation, many equivalents of the specific embodiments of the invention described herein. Such equivalents are intended to be/encompassed by the following claims.

What is claimed is:

1. A method of treating a xenogeneic subject suffering from a disorder characterized by decreased liver function, comprising
   i) isolating a population of porcine hepatocytes
   ii) altering the hepatocytes by contacting the hepatocytes prior to introduction into a subject with at least one anti-MAC class I antibody, which binds to the MHC class I antigen on the cell surface but does not activate complement or induce lysis of the cells such that rejection of the hepatocytes is inhibited upon introduction of the cells into the xenogeneic subject; and
   iii) administering the porcine hepatocytes to the liver of the subject while decreasing portal blood pressure of the subject to thereby treat a xenogeneic subject suffering from a disorder characterized by decreased liver function.

2. The method of claim 1, wherein the porcine hepatocytes are obtained from an embryonic pig.

3. The method of claim 1, wherein the subject is a human.

4. The method of claim 1, wherein the disorder is a genetic disease involving a liver enzyme.

5. The method of claim 4, wherein the genetic disease is Crigler-Najjar Syndrome Type I or ornithine transcarbamoylase deficiency.

6. The method of claim 1, wherein the disorder is a genetic disease involving a protein secreted by the liver.

7. The method of claim 6, wherein the genetic disease is hereditary emphysema or hemophilia.

8. The method of claim 1, wherein the disorder is acute liver failure.

9. The method of claim 1, wherein the disorder is chronic liver failure.

10. The method of claim 1, wherein the disorder is hepatitis A, hepatitis B, or non-A, non-B hepatitis.

11. The method of claim 1, wherein the step of decreasing portal blood pressure comprises using a transjugular intra-hepatic porto-systemic shunt to decrease portal blood pressure.

12. The method of claim 1, further comprising administering an immunosuppressive agent to the subject.

13. The method of claim 1, wherein the porcine hepatocytes are free from at least one organism selected from the group consisting of parasites, bacteria, mycoplasma, and viruses.

14. The method of claim 1, wherein the disorder is familial hypercholesterolemia.

15. A method of treating a xenogeneic subject suffering from a disorder characterized by decreased liver function, comprising
  i) isolating a population of porcine hepatocytes
  ii) altering said porcine hepatocytes by contacting the hepatocytes prior to introduction into a subject with monoclonal antibody PT85, which binds to the MHC class I antigen on the cell surface but does not activate complement or induce lysis of the hepatocytes such that rejection of the cells is inhibited upon introduction of the hepatocytes into the xenogeneic subject; and
  iii) administering the porcine hepatocytes to the liver of the subject while decreasing portal blood pressure of the subject to thereby treat a xenogeneic subject suffering from a disorder characterized by decreased liver function.

16. A method of treating a xenogeneic subject suffering from a disorder characterized by decreased liver function, comprising
  i) isolating a population of porcine hepatocytes
  ii) altering the porcine hepatocytes by contacting the hepatocytes prior to introduction into a subject with at least one F(ab')2 fragment of an anti-MHC class I antibody, which binds to the MHC class I antigen on the cell surface but does not activate complement or induce lysis of the hepatocytes such that rejection of the hepatocytes is inhibited upon introduction of the hepatocytes into the xenogeneic subject;
  iii) administering the porcine hepatocytes to the liver of the subject while decreasing portal blood pressure of the subject to thereby treat a xenogeneic subject suffering from a disorder characterized by decreased liver function.

17. The method of claim 16, wherein the porcine hepatocytes are obtained from an embryonic pig.

18. The method of claim 16, wherein the subject is a human.

19. The method of claim 16, wherein the disorder is a genetic disease involving a liver enzyme.

20. The method of claim 16, wherein the genetic disease is Crigler-Najjar Syndrome Type I or ornithine transcarbamoylase deficiency.

21. The method of claim 16, wherein the disorder is a genetic disease involving a protein secreted by the liver.

22. The method of claim 16, wherein the genetic disease is hereditary emphysema or hemophilia.

23. The method of claim 16, wherein the disorder is acute liver failure.

24. The method of claim 16, wherein the disorder is chronic liver failure.

25. The method of claim 16, wherein the disorder is hepatitis A, hepatitis B, or non-A, non-B hepatitis.

26. The method of claim 16, wherein the disorder is familial hypercholesterolemia.

27. The method of claim 16, wherein the step of decreasing portal blood pressure comprises using a transjugular intra-hepatic porto-systemic shunt to decrease portal blood pressure.

28. The method of claim 16, further comprising administering an immunosuppressive agent to the subject.

29. The method of claim 16, wherein the porcine hepatocytes are free from at least one organism selected from the group consisting of parasites, bacteria, mycoplasma, and viruses.

* * * * *

UNITED STATES PATENT AND TRADEMARK OFFICE
CERTIFICATE OF CORRECTION

PATENT NO. : 6,610,288 B1
APPLICATION NO. : 08/653059
DATED : August 26, 2003
INVENTOR(S) : Albert Edge, Ryan Gunsalus and Nezam H. Afdhal It is certified that error appears in the above-identified patent and that said Letters Patent is hereby corrected as shown below:

Column 40, Claim 1 ii) "...prior to introduction into a subject with at least one anti-MAC class I antibody, which binds to the MHC class I antigen on the cell surface..." should read --...prior to introduction into a subject with at least one anti- MHC class I antibody, which binds to the MHC class I antigen on the cell surface...--

Signed and Sealed this

Seventeenth Day of October, 2006

JON W. DUDAS
*Director of the United States Patent and Trademark Office*